US009940714B2

(12) United States Patent
Ooga et al.

(10) Patent No.: US 9,940,714 B2
(45) Date of Patent: Apr. 10, 2018

(54) IMAGE ANALYZING DEVICE, IMAGE ANALYZING METHOD, AND COMPUTER PROGRAM PRODUCT

(71) Applicant: Kabushiki Kaisha Toshiba, Minato-ku (JP)

(72) Inventors: Junichiro Ooga, Kawasaki (JP); Kenji Hirohata, Koto (JP); Shinya Higashi, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/584,218

(22) Filed: May 2, 2017

(65) Prior Publication Data
US 2017/0236279 A1 Aug. 17, 2017

Related U.S. Application Data

(63) Continuation of application No. 14/943,134, filed on Nov. 17, 2015, now Pat. No. 9,675,293.

(30) Foreign Application Priority Data

Nov. 19, 2014 (JP) ................................. 2014-234537

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0033* (2013.01); *A61B 5/4528* (2013.01);
(Continued)

(58) Field of Classification Search
CPC ..... A61B 5/4528; A61B 5/0033; G06T 7/136; G06T 7/11; G06T 19/00; G06T 2207/3008; G06T 2210/41; G01N 3/08; G06K 9/46
See application file for complete search history.

(56) References Cited

U.S. PATENT DOCUMENTS 7,184,814 B2 2/2007 Lang
8,036,729 B2 10/2011 Lang
(Continued)

FOREIGN PATENT DOCUMENTS

JP 2005-185767 A 7/2005
JP 2006-263241 A 10/2006
(Continued)

*Primary Examiner* — Shefali Goradia
(74) *Attorney, Agent, or Firm* — Oblon, McClelland, Maier & Neustadt, L.L.P.

(57) ABSTRACT

According to an embodiment, an image analyzing device includes a first acquirer, a constructor, a first calculator, a second calculator, and a third calculator. The first acquirer is configured to acquire image information on a joint of a subject and bones connected to the joint. The constructor is configured to construct a three-dimensional shape of the bones and the joint, and relation characteristics between a load and deformation in the bones and the joint from the image information. The first calculator is configured to calculate a positional relation between the bones connected to the joint. The second calculator is configured to calculate acting force of a muscle acting on the bones connected to the joint based on the positional relation. The third calculator is configured to calculate first stress acting on the joint based on the three-dimensional shape, the relation characteristics, and the acting force.

10 Claims, 18 Drawing Sheets

(51) Int. Cl.
  *G06K 9/46* (2006.01)
  *G01N 3/08* (2006.01)
  *A61B 5/00* (2006.01)
  *G06T 19/00* (2011.01)
  *G06T 7/11* (2017.01)
  *G06T 7/136* (2017.01)
  *G06T 17/20* (2006.01)

(52) U.S. Cl.
  CPC .............. *G01N 3/08* (2013.01); *G06K 9/46* (2013.01); *G06T 7/11* (2017.01); *G06T 7/136* (2017.01); *G06T 17/20* (2013.01); *G06T 19/00* (2013.01); *G06T 2207/30008* (2013.01); *G06T 2210/41* (2013.01)

(56) References Cited

U.S. PATENT DOCUMENTS

| | | | |
|---|---|---|---|
| 2007/0015995 | A1 | 1/2007 | Lang |
| 2007/0173815 | A1 | 7/2007 | Murase |
| 2010/0292963 | A1* | 11/2010 | Schroeder ................. A61F 2/30 703/1 |
| 2013/0332128 | A1 | 12/2013 | Miles et al. |

FOREIGN PATENT DOCUMENTS

| | | | |
|---|---|---|---|
| JP | 2011-172977 A | 9/2011 | |
| JP | 2014-93052 A | 5/2014 | |
| JP | 2014-516594 A | 7/2014 | |

\* cited by examiner

IMAGE ANALYZING DEVICE, IMAGE ANALYZING METHOD, AND COMPUTER PROGRAM PRODUCT

CROSS-REFERENCE TO RELATED APPLICATION

This application is a continuation application of U.S. application Ser. No. 14/943,134, filed Nov. 17, 2015 which is based upon and claims the benefit of priority from Japanese Patent Application No. 2014-234537, filed on Nov. 19, 2014. The entire contents of the above-identified applications are incorporated herein by reference.

FIELD

Embodiments described herein relate generally to an image analyzing device, an image analyzing method, and a computer program product.

BACKGROUND

Widely known are technologies for estimating a three-dimensional positional relation between bones from a two-dimensional image obtained by capturing a joint with plain X-rays prior to surgery of osteoarthritis developing in a knee joint, a hip joint, and the like.

Japanese Patent Application Laid-open No. 2006-263241, for example, discloses a method for generating an evaluation function including relative fitness between a patient's skeleton and an implant component based on a computed tomography (CT) image or a magnetic resonance (MR) image. Japanese Patent Application Laid-open No. 2006-263241 also discloses a method for using the evaluation function to select an implant appropriate for the patient and make a surgical plan.

Actual human bones are subjected to muscle tension generated by a muscle attached to them, and the muscle tension changes stress acting on a joint. The conventional technology, however, does not estimate the stress with the acting force of the muscle taken into consideration, thereby failing to accurately calculate the stress acting on a joint of an actual patient.

DETAILED DESCRIPTION

According to an embodiment, an image analyzing device includes a first acquirer, a constructor, a first calculator, a second calculator, and a third calculator. The first acquirer is configured to acquire image information on a joint of a subject and bones connected to the joint. The constructor is configured to construct a three-dimensional shape of the bones and the joint, and relation characteristics between a load and deformation in the bones and the joint from the image information. The first calculator is configured to calculate a positional relation between the bones connected to the joint. The second calculator is configured to calculate acting force of a muscle acting on the bones connected to the joint based on the positional relation. The third calculator is configured to calculate first stress acting on the joint based on the three-dimensional shape, the relation characteristics, and the acting force.

First Embodiment

Exemplary embodiments of an image analyzing device, an image analyzing method, and a computer program are described below in greater detail with reference to the accompanying drawings.

Figure 1:
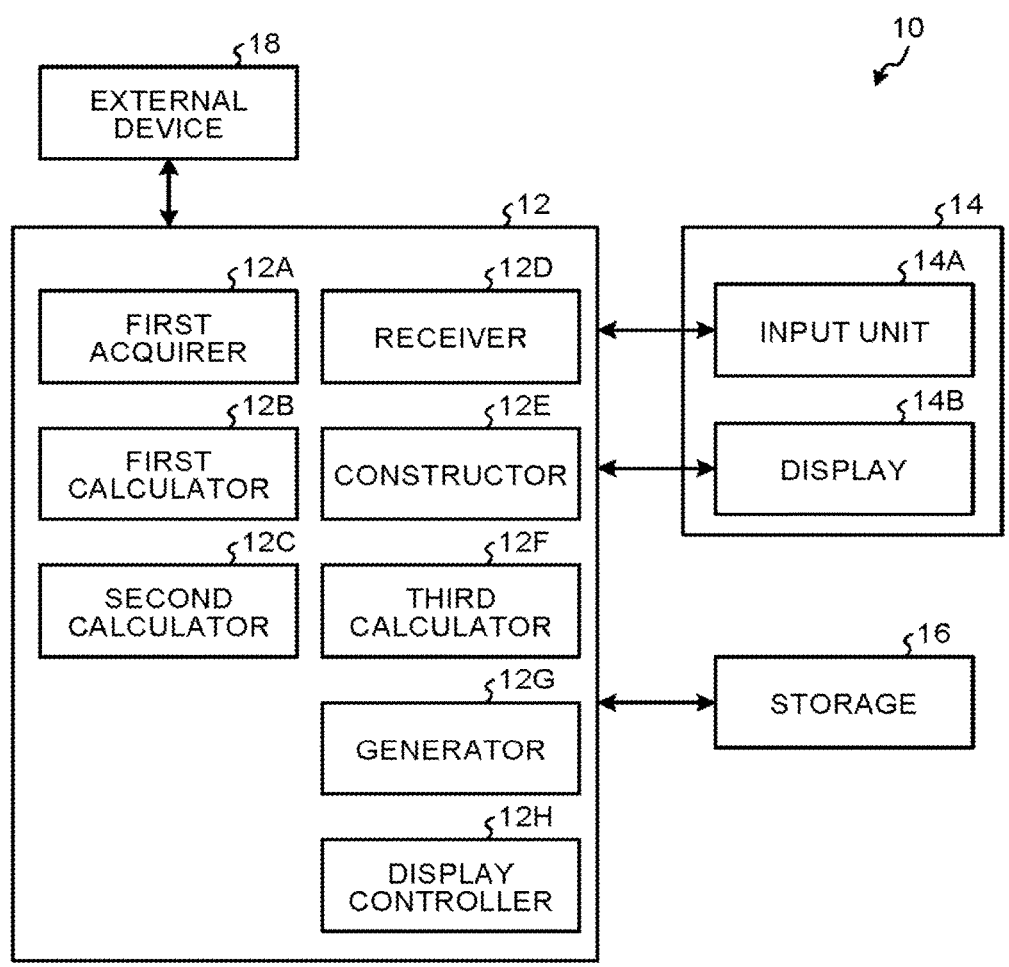
FIG. 1 is a configuration diagram of an image analyzing device.

FIG. 1 is a configuration diagram of an image analyzing device 10 according to an embodiment. The image analyzing device 10 according to the present embodiment analyzes a joint of a subject.

The image analyzing device 10 is connected to an external device 18. The external device 18 provides image information to be analyzed by the image analyzing device 10. The image information to be analyzed is image information on a joint of a subject and bones connected to the joint. Specifically, the image information to be analyzed includes a joint of the subject, bones connected to the joint, and a muscle. The muscle includes a muscular tissue.

The external device 18, for example, scans the subject using X-rays or magnetism, thereby obtaining time-series computed tomography (CT) image information or time-series magnetic resonance (MR) image information of the subject. The image analyzing device 10 may include the external device 18.

The following describes a case where the image information to be analyzed according to the present embodiment is CT image information. The image information to be analyzed is not limited to CT image information. The image information to be analyzed may be MR image information or ultrasonic echo image information, for example.

The CT image information may be slice data indicating two-dimensional spatial distribution of CT values or volume data indicating three-dimensional spatial distribution of CT values. In the following description, the CT image information is volume data. The external device 18 outputs time-series CT image information to the image analyzing device 10. The image analyzing device 10 may acquire the CT image information to be analyzed from another device or a storage that stores therein time-series CT images, for example. The image information to be analyzed by the image analyzing device 10 is not limited to time-series images. In the following description, the image information to be analyzed is simply referred to as an image or a CT image.

The image analyzing device 10 includes a controller 12, a user interface (UI) 14, and a storage 16. The UI 14 and the storage 16 are connected to the controller 12 in a manner transmitting and receiving data and signals thereto and therefrom. The controller 12 is connected to the external device 18.

The UI 14 includes an input unit 14A and a display 14B. The input unit 14A receives various instructions and information from a user. The input unit 14A is a keyboard, a mouse, a switch, or a microphone, for example.

The display 14B displays various types of information, such as a CT image and an analysis result. The display 14B is a cathode-ray tube (CRT) display, a liquid-crystal display, an organic electroluminescence (EL) display, or a plasma display, for example.

The UI 14 may have a touch panel function provided with the input unit 14A and the display 14B integrally.

The storage 16 includes various types of storage media, such as a hard disk drive, and stores therein various types of data, such as time-series CT images. The storage 16, for example, stores therein the time-series CT images in a medical image file format conforming to digital imaging and communications in medicine (DICOM). The storage 16 may store therein medical data acquired by the controller 12 or the like in a manner associated with the time-series CT images.

The controller 12 controls the image analyzing device 10. The controller 12 includes a first acquirer 12A, a first calculator 12B, a second calculator 12C, a receiver 12D, a constructor 12E, a third calculator 12F, a generator 12G, and a display controller 12H. A part or all of the first acquirer 12A, the first calculator 12B, the second calculator 12C, the receiver 12D, the constructor 12E, the third calculator 12F, the generator 12G, and the display controller 12H may be provided by a processor, such as a central processing unit (CPU), executing a computer program, that is, as software. Alternatively, a part or all of them may be provided as hardware, such as an integrated circuit (IC), or a combination of software and hardware.

The first acquirer 12A acquires an image relating to a joint of a subject and bones connected to the joint. The first acquirer 12A according to the present embodiment acquires a CT image from the external device 18, thereby acquiring an image relating to a joint of a subject and bones connected to the joint (hereinafter, referred to as a CT image). The storage 16 may store therein CT images of the subject in advance. In this case, the first acquirer 12A reads a CT image of the subject to be analyzed from the storage 16, thereby acquiring the CT image.

The first acquirer 12A outputs the acquired CT image to the first calculator 12B and the constructor 12E.

The constructor 12E constructs a three-dimensional shape of the bones and the joint, and relation characteristics between a load and deformation of the bones and the joint from the CT image acquired by the first acquirer 12A.

The constructor 12E according to the present embodiment, for example, constructs a first mechanical model indicating at least the three-dimensional shape of the bones and the joint and the relation characteristics between a load and deformation. The first mechanical model is data obtained by adding the relation characteristics between a load and deformation of the bones and the joint to a bone-and-joint shape model indicating the three-dimensional shape of the bones and the joint, for example. The relation characteristics between a load and deformation indicate the relation of deformation with a load. The relation characteristics between a load and deformation are hardness, for example.

In the following description, the relation characteristics between a load and deformation may be simply referred to as "hardness" to simplify the explanation. The "hardness" according to the present embodiment, however, is given by way of example of the relation characteristics between a load and deformation, and the relation characteristics are not limited thereto.

Specifically, the constructor 12E extracts a bone region from the CT image acquired by the first acquirer 12A. In a case where the image to be analyzed is a CT image, for example, hard bones have a CT value of approximately 1000 HU; whereas soft tissues corresponding to connective tissues other than bones, such as tendons, ligaments, and muscles, have a CT value of approximately 0 to 100 HU. The constructor 12E sets in advance a threshold of the CT value for discriminating bones from soft tissues. The threshold may be adjusted by an operation performed by the user on the input unit 14A, for example.

The constructor 12E extracts a region having a CT value of equal to or larger than the threshold from the CT image acquired by the first acquirer 12A. Thus, the constructor 12E extracts a joint region and a bone region to generate a bone-and-joint shape model indicating the three-dimensional shape of the joint and the bones.

In a case where the image analyzing device 10 analyzes the structure of the joint by performing a numerical analysis using the finite element method (FEM), for example, the constructor 12E generates a three-dimensional finite element model as the bone-and-joint shape model of the joint and the bones. The FEM is a method for approximating deformation by dividing a region to be analyzed into mesh-like regions (referred to as elements) surrounded by nodes.

The constructor 12E generates the first mechanical model by adding the relation characteristics between a load and deformation of the bones and the joint to the bone-and-joint shape model. The CT value varies depending on physical properties. To address this, the constructor 12E calculates the relation characteristics between a load and deformation, such as the hardness of the bones and the joint, of each element based on the CT value. The constructor 12E adds the relation characteristics to each element at a corresponding position on the bone-and-joint shape model, thereby generating the first mechanical model. The constructor 12E may perform filtering to remove a discontinuous portion from the generated shape model.

Displacement includes displacement caused by rigid-body displacement and displacement caused by material deformation in each portion. The constructor 12E may separate displacement caused by rigid-body displacement from displacement caused by material deformation in each portion to calculate the relation characteristics between a load and deformation of each element.

Specifically, the constructor 12E may further construct second relation characteristics between a load and deformation of a living tissue other than the bones or the joint that is hardly deformed by a factor other than loads and from which deformation caused by a load can be extracted. Examples of the factor other than loads include, but are not limited to, the degree of congestion with blood in a muscle fiber and a sliding motion of filaments constituting a muscle fiber. Examples of the living tissue include, but are not limited to, a tendon, a ligament, and a cartilage.

In this case, the constructor 12E calculates the amount of deformation of a tendon, a ligament, and a cartilage connected or attached to the bones or the joint included in the CT image by an image analysis and a tracking technology. The constructor 12E then calculates the relation characteristics (second relation characteristics) between a load and deformation of each element. The constructor 12E adds the relation characteristics of the bones and the joint and the second relation characteristics of the living tissue, such as a tendon, a ligament, and a cartilage, to each element at a corresponding position on the bone-and-joint shape model, thereby constructing the first mechanical model.

Figure 2:
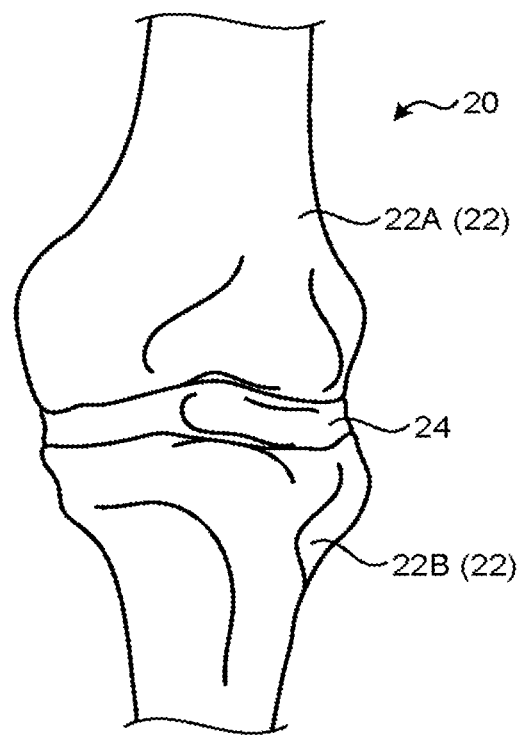
FIG. 2 is a schematic of a first mechanical model.

FIG. 2 is a schematic of an example of a first mechanical model 20. The first mechanical model 20 is data obtained by adding the relation characteristics between a load and deformation of a joint 24 and bones 22 to a bone-and-joint shape model indicating the three-dimensional shape of the joint 24 and a bone 22A and a bone 22B collectively referred to as the bones 22 connected to the joint 24.

Referring back to FIG. 1, the constructor 12E according to the present embodiment calculates the relation characteristics between a load and deformation, such as the hardness of the bones and the joint, based on the CT value. The constructor 12E adds the relation characteristics to each element at a corresponding position on the bone-and-joint shape model, thereby generating the first mechanical model.

The following describes an example of a method for calculating the relation characteristics between a load and deformation of each element performed by the constructor 12E.

The constructor 12E sets a load condition to the tendon and the bone end for the bones and the joint (which may include a living tissue, such as a tendon, a ligament, and a cartilage). The constructor 12E sets a displacement boundary condition to the bone end (end of the bones) and the joint. The constructor 12E sets a material constitution equation to each living tissue. The constructor 12E performs a large deformation and stress analysis based on the continuum mechanics (reference: Y. C. Fung, First Course in Continuum Mechanics (3rd Edition)).

The large deformation and stress analysis, for example, is a method for numerically calculating the physical quantity of stress, strain, pressure, and deformation on each portion and a temporal change in the physical quantity by discretizing an equation of the continuum mechanics with the FEM. The large deformation and stress analysis is not limited to an elastic analysis of isotropic deformation and may be an analysis using a homogenization method with anisotropic deformation characteristics of the bones taken into consideration. Alternatively, the large deformation and stress analysis may be a non-linear analysis, a static analysis, or a dynamic analysis with inelastic deformation characteristics and time-dependent deformation characteristics of the living tissue taken into consideration.

The constructor 12E calculates the relation characteristics between a load and deformation of each element in the bones and the joint by performing the large deformation and stress analysis based on the CT image acquired by the first acquirer 12A. The constructor 12E further constructs (calculates), by an image analysis and a tracking technology, the second relation characteristics between a load and deformation of a living tissue other than the bones or the joint (e.g., a tendon, a ligament, and a cartilage) that is hardly deformed by a factor other than loads and from which deformation caused by a load can be extracted. The constructor 12E adds the calculated relation characteristics and the calculated second relation characteristics to each element at a corresponding position on the bone-and-joint shape model, thereby generating the first mechanical model.

The constructor 12E may add the relation characteristics to each element at a corresponding position on the bone-and-joint shape model to construct the first mechanical model (not including the second relation characteristics). The constructor 12E preferably constructs the first mechanical model including the second relation characteristics to improve the accuracy of the calculation of first stress, which will be described later.

Referring back to FIG. 1, the first calculator 12B calculates the positional relation between the bones connected to the joint using the CT image received from the first acquirer 12A.

The positional relation between the bones connected to the joint includes an angle (joint angle) formed around the joint by the bones connected to the joint, a bone-centered coordinate system, the moment of inertia, the mass of the bones, and the muscle Jacobian, for example.

The first calculator 12B according to the present embodiment calculates the positional relation using the CT image received from the first acquirer 12A, thereby generating a musculoskeletal model.

The musculoskeletal model is obtained by arranging the three-dimensional shape of the muscle to the bone-and-joint shape model indicating the three-dimensional shape of the joint and the bones and adding the positional relation thereto. The musculoskeletal model may be further provided with the three-dimensional shape of a ligament and a tendon, for example. The muscle according to the present embodiment is a muscle coupled to the two bones connected to the joint. The muscle starts from a start portion on a first bone and ends at an end portion on a second bone.

The musculoskeletal model indicates at least the positional relation between the joint and the bones connected to the joint. The musculoskeletal model may further include the hardness, the weight, and the like of the bones, the joint, and the muscle coupled to the bones.

The first calculator 12B generates a musculoskeletal model from the CT image using the following method.

Specifically, similarly to the constructor 12E, the first calculator 12B extracts a region having a CT value of equal to or larger than the threshold from the CT image acquired by the first acquirer 12A. Thus, the first calculator 12B extracts the joint region and the bone region to generate a bone-and-joint shape model indicating the three-dimensional shape of the joint and the bones. The first calculator 12B extracts a region having a CT value of a soft tissue (muscle) from the CT image, thereby extracting a muscle region, and arranges the three-dimensional shape of the muscle on the bone-and-joint shape model.

The first calculator 12B further calculates the positional relation between the joint and the bones connected to the joint, such as the joint angle, the bone-centered coordinate system, the moment of inertia, the mass of the bones, and the muscle Jacobian, from the CT image.

The first calculator 12B, for example, extracts several points having a characteristic shape in the bones and the joint from the generated bone-and-joint shape model. The first calculator 12B derives a coordinate system centering on the positions of the center of gravity of the points as the respective centered coordinate systems of the bones and the joint.

The first calculator 12B calculates the moment of inertia I using Equation (1) below around the axis of each calculated centered coordinate system of the bones and the joint.

$$I = \Sigma m_i r_i^2 \quad (1)$$

In Equation (1), I denotes the moment of inertia, $m_i$ denotes the mass of an element in a case where the bones and the joint are segmented into mesh, and $r_i$ denotes the distance to the coordinate axis. The mass of an element is calculated based on the standard density and the volume of the element stored in advance, and $r_i$ is calculated based on the bone-and-joint shape model.

The first calculator 12B calculates the joint angle by transforming the coordinate systems of the adjacent two bones connected to the joint. Given $T_a$ is the coordinate system (homogeneous transformation matrix) of the proximal bone, and $T_b$ is the homogeneous transformation matrix indicating the coordinate system of the distal bone, for example, Equation (2) below is satisfied. These coordinate systems are calculated by the bone-and-joint shape model.

$$T = T_b T_a^{-1} \qquad (2)$$

The first calculator 12B uses Equation (2) to compare the matrix rotated by $\alpha$, $\beta$, and $\gamma$ about the X-axis, the Y-axis, and the Z-axis, respectively, with T, thereby calculating joint angles $\alpha$, $\beta$, and $\gamma$ (definition of Euler angles).

The first calculator 12B calculates the muscle Jacobian using Equation (3) below.

$$L = dl/d\theta \qquad (3)$$

In Equation (3), L denotes the muscle Jacobin, dl denotes a minute amount of change in the muscle length, and $d\theta$ denotes a minute change in the joint angle. Here, dl and $d\theta$ may be predetermined values or may be calculated based on the geometric relation between the muscle and the center of the joint extracted from the CT image.

Standard values of the moment of inertia, the mass of the bones and the joint, and the muscle Jacobian may be calculated in advance by the controller 12 and stored in the storage 16 as a standard positional relation. The first calculator 12B may use the moment of inertia, the mass of the bones and the joint, and the muscle Jacobian stored in the storage 16. When the first calculator 12B newly calculates at least one of the moment of inertia, the mass of the bones, the mass of the joint, and the muscle Jacobian, the first calculator 12B may store the value resulting from the calculation as a new value in the storage 16. Thus, the first calculator 12B updates the storage 16.

The first calculator 12B arranges the three-dimensional shape of the muscle on the bone-and-joint shape model indicating the three-dimensional shape of the joint and the bones. The first calculator 12B adds the calculated positional relation (the joint angle, the bone-centered coordinate system, the moment of inertia, the mass of the bones and the joint, and the muscle Jacobian) to the obtained bone-and-joint shape model, thereby generating a musculoskeletal model.

The first calculator 12B generates a musculoskeletal model from time-series CT images, thereby generating a time-series musculoskeletal model. Specifically, the first calculator 12B generates a time-series musculoskeletal model, making it possible to calculate a change in the joint angle and a change in the muscle length based on a temporal change in the position of the bones extracted from the CT images acquired in time series.

The second calculator 12C calculates acting force of the muscle acting on the bones connected to the joint based on the positional relation calculated by the first calculator 12B.

The acting force includes at least one of muscle tension of the muscle coupled to the bones connected to the joint and torque acting on the joint, for example. The muscle coupled to the bones connected to the joint is a muscle coupled to the two bones connected to the joint, starting from the start portion on the first bone and ending at the end portion on the second bone.

Specifically, the second calculator 12C performs inverse dynamic calculation based on the positional relation calculated by the first calculator 12B, thereby calculating acting force of the muscle acting on the joint.

To perform inverse dynamic calculation, the positional relation between the joint and the bones connected to the joint is required, including the joint angle, the bone-centered coordinate system, the moment of inertia, the mass of the bones, and the muscle Jacobian. The second calculator 12C acquires the joint angle, the bone-centered coordinate system, the moment of inertia, the mass of the bones, and the muscle Jacobian from the musculoskeletal model calculated by the first calculator 12B.

The second calculator 12C uses the joint angle, the bone-centered coordinate system, the moment of inertia, the mass of the bones, and the muscle Jacobian to perform inverse dynamic calculation by Equations (4) to (6) below. Thus, the second calculator 12C calculates the acting force of the muscle acting on the joint. Equation (4) below is an equation of the torque acting on the joint.

The equation of motion at each joint is expressed by Equation (4).

$$\tau = M d^2\theta/dt^2 + D d\theta/dt + G(\theta) \qquad (4)$$

In Equation (4), $\tau$ denotes the torque acting on the joint, $\theta$ denotes the joint angle, $d\theta/dt$ denotes joint angular velocity, $d^2\theta/dt^2$ denotes joint angular acceleration, M denotes the moment of inertia, D denotes viscosity resistance, and $G(\theta)$ denotes a gravity term (which varies depending on the posture).

The second calculator 12C calculates the joint angular velocity ($d\theta/dt$) by calculating the angular velocity of the joint angle with the time-series musculoskeletal model calculated by the first calculator 12B. The second calculator 12C calculates the joint angular acceleration ($d^2\theta/dt^2$) by calculating the angular velocity of the joint angle with the time-series musculoskeletal model calculated by the first calculator 12B. The viscosity resistance (D) can be measured in advance and stored in the storage 16. The second calculator 12C calculates the gravity term ($G(\theta)$) based on the mass of the bones and the position of the center of gravity.

In a case where the CT image acquired by the first acquirer 12A is not time-series images (that is, a one-shot CT image), the second calculator 12C fails to obtain the item relating to a temporal change in Equation (4). In this case, the second calculator 12C performs processing using $\tau = G(\theta)$.

The second calculator 12C performs inverse dynamic calculation, thereby calculating the muscle tension of the muscle coupled to the bones connected to the joint.

In a case where an applied load F acts on the joint, Equation (5) below is satisfied based on the principle of virtual work.

$$J^T F + \tau = L^T m \qquad (5)$$

$$m = (L^T)^{-1}(J^T F + \tau) \qquad (6)$$

In Equations (5) and (6), J denotes the joint angle Jacobian (differential relation between the position and the joint angle), L denotes the muscle Jacobian (differential relation between the joint angle and the muscle length), and m denotes the muscle tension. By multiplying the left-hand side of Equation (5) by an inverse matrix of $L^T$ (refer to Equation (6)), the second calculator 12C calculates the muscle tension m.

The second calculator 12C derives the joint angle Jacobian (J) in Equations (5) and (6) by partially differentiating the applied load (vector) with respect to the joint angle (vector).

As described above, the second calculator 12C performs inverse dynamic calculation based on the positional relation (musculoskeletal model) calculated by the first calculator 12B. Thus, the second calculator 12C calculates the acting force of the muscle acting on the joint (e.g., the muscle tension and the torque acting on the joint).

The second calculator 12C may calculate the acting force by assuming a viscoelastic model simulating an actual muscle as a muscle physical model.

The following describes the third calculator 12F.

The third calculator 12F calculates the first stress acting on the joint based on the three-dimensional shape and the relation characteristics constructed by the constructor 12E and the acting force calculated by the second calculator 12C. The third calculator 12F according to the present embodiment calculates the first stress acting on the joint based on the first mechanical model constructed by the constructor 12E and the acting force calculated by the second calculator 12C. In other words, the third calculator 12F calculates the first stress of each element (each element in the FEM) on the contact surface between the bones and the joint.

Specifically, the third calculator 12F sets the muscle tension and the torque acting on the joint calculated in the inverse dynamic calculation performed by the second calculator 12C as a boundary condition of an external load for the first mechanical model. Thus, the third calculator 12F analyzes the structure of the joint, thereby calculating the first stress acting on the cartilage serving as the contact surface between the bones and the joint. To calculate the first stress, the third calculator 12F performs a numerical analysis using the known FEM.

The third calculator 12F calculates the first stress of each element on the contact surface between the bones and the joint, thereby deriving distribution of the first stress acting on the joint (that is, the contact surface between the bones and the joint).

The generator 12G generates an analysis image including a first stress image indicating the first stress acting on the joint calculated by the third calculator 12F. The first stress image indicates a stress region on which the first stress acts on the contact surface between the bones and the joint of the subject with color density corresponding to the intensity of the first stress. The color density according to the present embodiment indicates at least one of the color and the density.

The generator 12G according to the present embodiment generates a stress image indicating a stress region on which the first stress acts on the contact surface between the bones and the joint with the color density corresponding to the intensity of the first stress. The generator 12G then arranges the stress image on a bone image indicating the three-dimensional shape of the bones, thereby generating the first stress image.

The receiver 12D receives various operating instructions issued by the user via the input unit 14A.

The display controller 12H performs control to display an analysis image 34 including a first stress image 30 generated by the generator 12G on the display 14B (refer to FIGS. 3 to 6).

Figure 3:
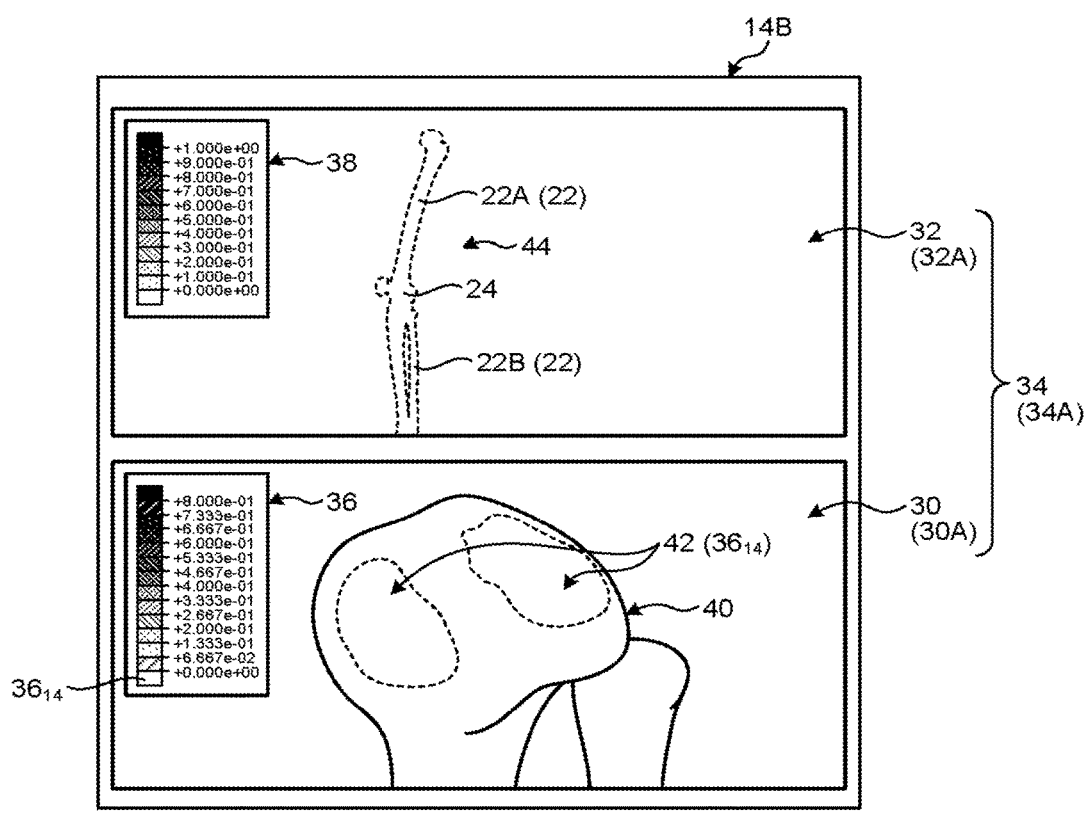
FIG. 3 is a schematic of an analysis image.

FIG. 3 is a schematic of an example of the analysis image 34. The analysis image 34 includes a first mechanical model image 32 and the first stress image 30, for example. The analysis image 34 includes at least the first stress image 30.

In a case where the analysis image 34 includes the first mechanical model image 32, the generator 12G generates the first mechanical model image 32, thereby generating the analysis image 34 including the first mechanical model image 32 and the first stress image 30.

The first stress image 30 indicates a bone image 40 and a stress region 42 on which the first stress acts on the contact surface between the bones and the joint with the color density corresponding to the intensity of the acting first stress. In the example illustrated in FIG. 3, the stress region 42 is represented by the color density indicating that the first stress is "0".

The first stress image 30 may further include a gauge 36 indicating the color density corresponding to the intensity of the first stress.

The gauge 36, for example, displays a list of color densities corresponding to the intensities of the first stress in a manner associated with the values of the first stress corresponding to the respective color densities. In the example illustrated in FIG. 3, the stress region 42 is represented by the color density ($36_{14}$) displayed by the gauge 36 and indicating that the first stress is "0". This configuration can facilitate the user's recognition that a first stress of "0" is acting on the stress region 42 by viewing the first stress image 30.

The analysis image 34 may include the first mechanical model image 32 indicating the first mechanical model. The first mechanical model image 32 includes a shape model image 44 and a gauge 38.

The shape model image 44 three-dimensionally indicates the positional relation between the bones and the joint when the distribution and the intensity of the first stress acting on the contact surface between the bones and the joint are those of the first stress indicated by the first stress image 30 included in the same analysis image 34.

The gauge 38 is an image displaying a list of color densities corresponding to the intensities of the relation characteristics between a load and deformation in a manner associated with the values of the relation characteristics corresponding to the respective color densities. The shape model image 44 is provided with the color density corresponding to the value of the relation characteristics between a load and deformation.

The generator 12G generates the analysis image 34 including the first stress image 30, whereby the display 14B displays the analysis image 34 illustrated in FIG. 3, for example. The image analyzing device 10 displays the first stress image 30 indicating the stress region 42 on which the first stress acts on the contact surface between the bones and the joint with the color density corresponding to the intensity of the first stress. Thus, the image analyzing device 10 can facilitate the user's recognition of the position and the range on which the first stress at various intensities acts on the contact surface between the bones and the joint.

The generator 12G generates the analysis image 34 including the first stress image 30 and the first mechanical model image 32, whereby the display 14B displays the analysis image 34 illustrated in FIG. 3, for example. Thus, the image analyzing device 10 can facilitate the user's recognition of the positional relation between the joint 24 and the bones 22 when the first stress indicated by the first stress image 30 is acting.

The generator 12G may change the positional relation between the joint 24 and the bones 22, thereby generating the first stress image 30 and the first mechanical model image 32 corresponding to the change in the positional relation.

The generator 12G, for example, controls the first calculator 12B, the constructor 12E, the second calculator 12C, and the third calculator 12F so as to calculate the first stress acting on the joint 24 when the positional relation between the joint 24 and the bones 22 changes the angle (joint angle) formed around the joint 24 by the two bones 22 connected to the joint 24 from 180° to 45°. The generator 12G acquires the distribution of the first stress corresponding to each joint angle from the third calculator 12F.

Let us assume a case where the time-series CT images acquired by the first acquirer 12A are images obtained by changing the joint angle (changing the joint angle from 180° to 45°, for example). In this case, the first calculator 12B, the second calculator 12C, the constructor 12E, and the third calculator 12F perform the processing described above using the time-series CT images acquired by the first acquirer 12A, thereby calculating the distribution of the first stress corresponding to each joint angle. In this case, the generator 12G acquires the distribution of the first stress corresponding to each joint angle from the third calculator 12F.

The generator 12G generates the first stress image 30 corresponding to each joint angle. The display controller 12H displays the analysis image 34 including the first stress image 30 generated by the generator 12G on the display 14B. The generator 12G may generate the first mechanical model image 32 to generate the analysis image 34 including the first stress image 30 and the first mechanical model image 32.

Figure 4:
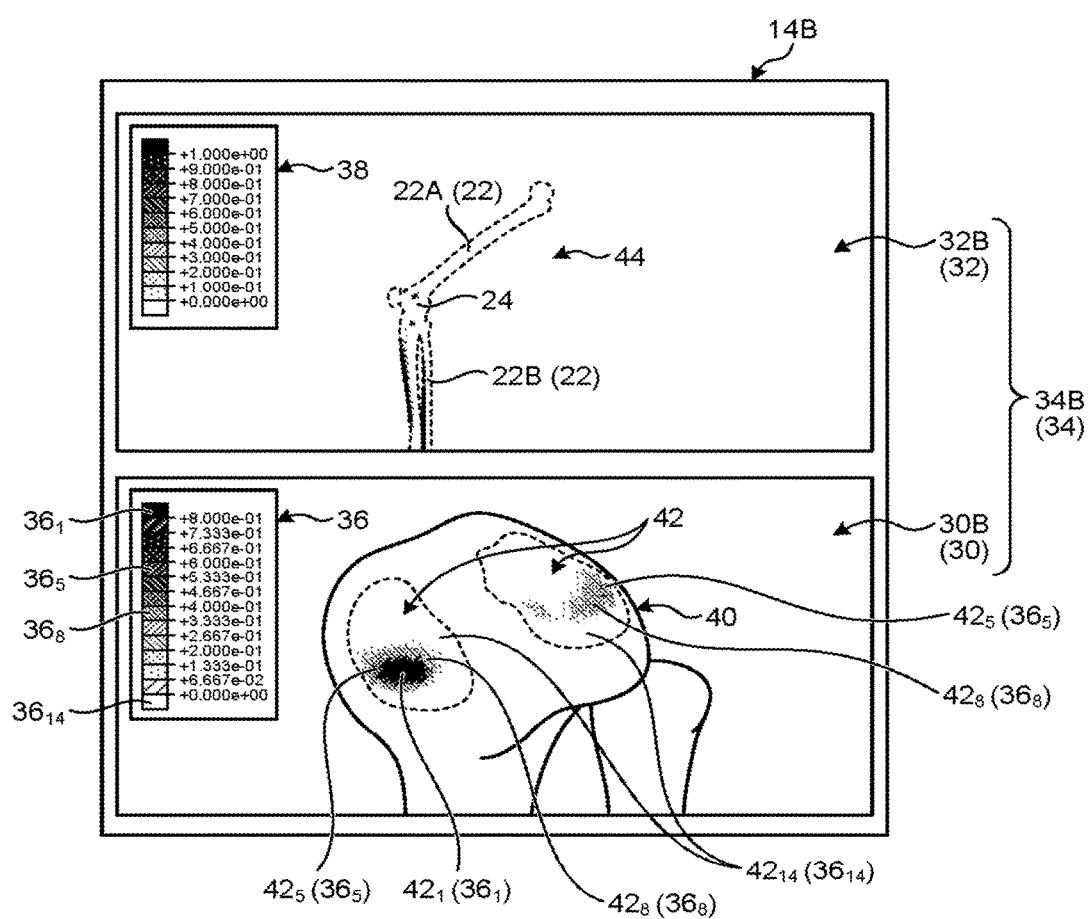
FIG. 4 is a schematic of another analysis image.
Figure 5:
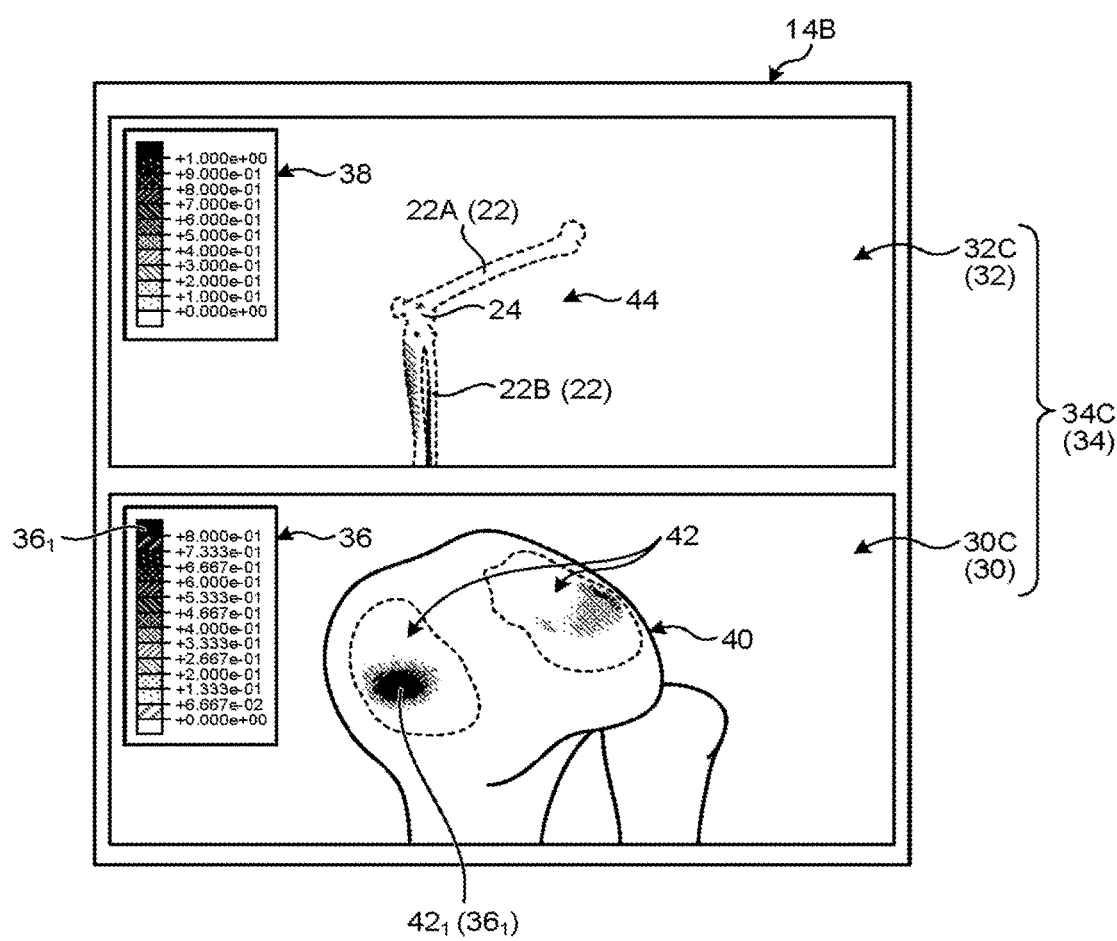
FIG. 5 is a schematic of still another analysis image.
Figure 6:
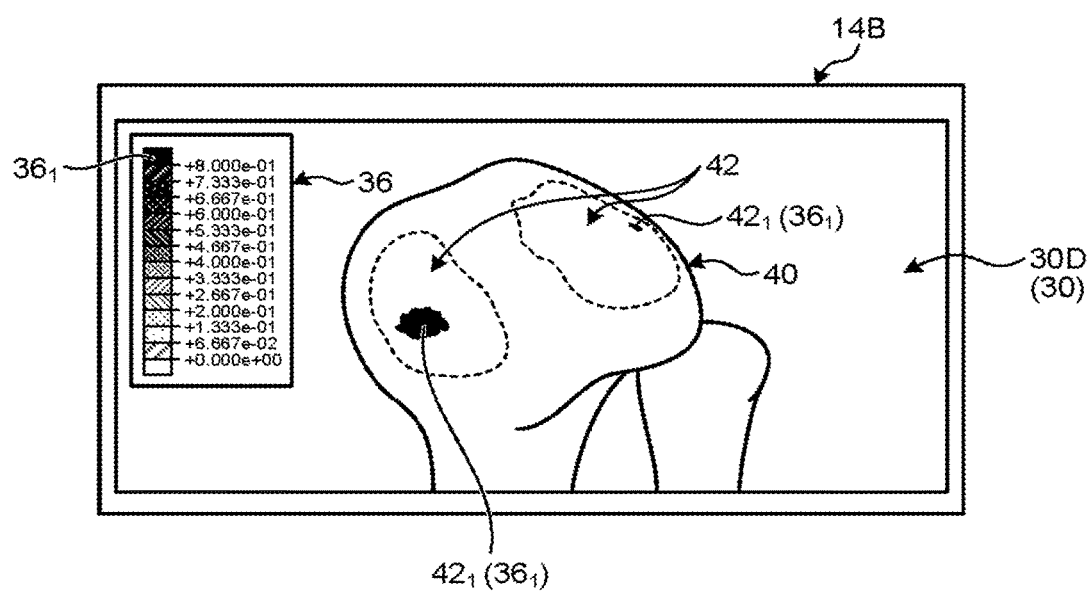
FIG. 6 is a schematic of still another analysis image.

In this case, the display controller 12H displays the analysis image 34 on the display 14B, thereby displaying the analysis images 34 illustrated in FIGS. 3 to 5 on the display 14B, for example.

FIG. 3 is a schematic of an example of an analysis image 34A including a first mechanical model image 32A and a first stress image 30A when the angle (joint angle) formed by the two bones 22A and 22B connected to the joint 24 is approximately 180°. In the example illustrated in FIG. 3, the stress region 42 is represented by the color density ($36_{14}$) indicating that the first stress is "0" in the gauge 36.

FIG. 4 is a schematic of an example of an analysis image 34B including a first mechanical model image 32B and a first stress image 30B when the angle (joint angle) formed by the two bones 22A and 22B connected to the joint 24 is approximately 120°. In the example illustrated in FIG. 4, a stress region $42_1$ on the contact surface between the bones and the joint is represented by a color density $36_1$ indicating a first stress of "$8 \times 10^{-1}$". A stress region $42_5$ is represented by a color density $36_5$ indicating a first stress of "$5.333 \times 10^{-1}$". A stress region $42_8$ is represented by a color density $36_8$ indicating a first stress of "$4.0 \times 10^{-1}$" A stress region $42_{14}$ positioned outermost is represented by a color density $36_{14}$ indicating a first stress of "0".

In FIG. 4, the first mechanical model image 32B included in the analysis image 34B indicates that the angle formed by the bone 22A and the bone 22B is approximately 120°.

FIG. 5 is a schematic of an example of an analysis image 34C including a first mechanical model image 32C and a first stress image 30C when the angle (joint angle) formed by the two bones 22A and 22B connected to the joint 24 is approximately 90°. Similarly to FIG. 4, the stress regions 42 in the example illustrated in FIG. 5 are represented by respective color densities corresponding to the intensities of the acting first stress. In comparison with the color density in the stress region 42 in FIG. 4, the stress region 42 in FIG. 5 has a larger area of higher first stress.

As described above, the generator 12G generates the first stress image 30 (first stress image 30A, 30B, or 30C) and the first mechanical model image 32 (first mechanical model image 32A, 32B, or 32C) depending on the change in the positional relation between the joint 24 and the bones 22. The display controller 12H displays the first stress image 30 (first stress image 30A, 30B, or 30C) and the first mechanical model image 32 (first mechanical model image 32A, 32B, or 32C) depending on the change in the positional relation on the display 14B.

Thus, the image analyzing device 10 can facilitate the user's recognition of the intensity of the first stress and the position and the range on which the first stress acts on the contact surface between the bones and the joint depending on the change in the positional relation between the joint 24 and the bones 22.

When the user performs an operation on the input unit 14A to input a joint angle, the generator 12G may generate the first stress image 30 and the first mechanical model image 32 corresponding to the input joint angle. The display controller 12H may display the analysis image 34 including the first stress image 30 and the first mechanical model image 32 generated correspondingly to the input joint angle on the display 14B. When the user performs an operation on the input unit 14A to instruct display of an analysis image resulting from the change in the positional relation, the display controller 12H may display the first stress images 30 and the first mechanical model images 32 generated correspondingly to the joint angle in a manner sequentially switched in descending order or ascending order of the joint angle on the display 14B.

The display controller 12H may display the first stress image 30 selectively including the stress region 42 of the first stress having intensity specified by the user on the display 14B.

Let us assume a case where, while the display controller 12H is displaying the analysis image 34 on the display 14B, the user issues an operating instruction via the input unit 14A to specify first stress having predetermined intensity indicated by the gauge 36, for example. The receiver 12D receives a signal indicating the intensity of the first stress specified by the user from the input unit 14A.

Upon receiving the signal indicating the intensity of the first stress from the input unit 14A while displaying the analysis image 34 including the first stress image 30 on the display 14B, the display controller 12H displays, on the display 14B, the first stress image 30 selectively indicating only the stress region 42 on which the first stress having the specified intensity acts out of the stress regions 42 in the first stress image 30 being displayed.

Let us assume a case where the user issues an operating instruction via the input unit 14A to specify a display region having color density of $36_1$ indicating a first stress of "$8 \times 10^{-1}$" in the gauge 36 while the first stress image 30C illustrated in FIG. 5 is being displayed on the display 14B, for example. In this case, the display controller 12H displays a first stress image 30D (refer to FIG. 6) on the display 14B. The first stress image 30D selectively indicates the stress region $42_1$ on which a first stress of "$8 \times 10^{-1}$" having the intensity corresponding to the color intensity $36_1$ acts on the contact surface between the bones and the joint.

The display controller 12H may highlight the stress region 42 of the first stress having the intensity specified by the user compared with the other regions.

The display controller 12H may display the first stress image 30 selectively including the stress region 42 of the first stress falling within an intensity range specified by the user on the display 14B. In this case, the display controller 12H displays, on the display 14B, the first stress image 30 selectively including the stress region 42 on which the first stress falling within the intensity range specified by the user acts.

Figure 7:
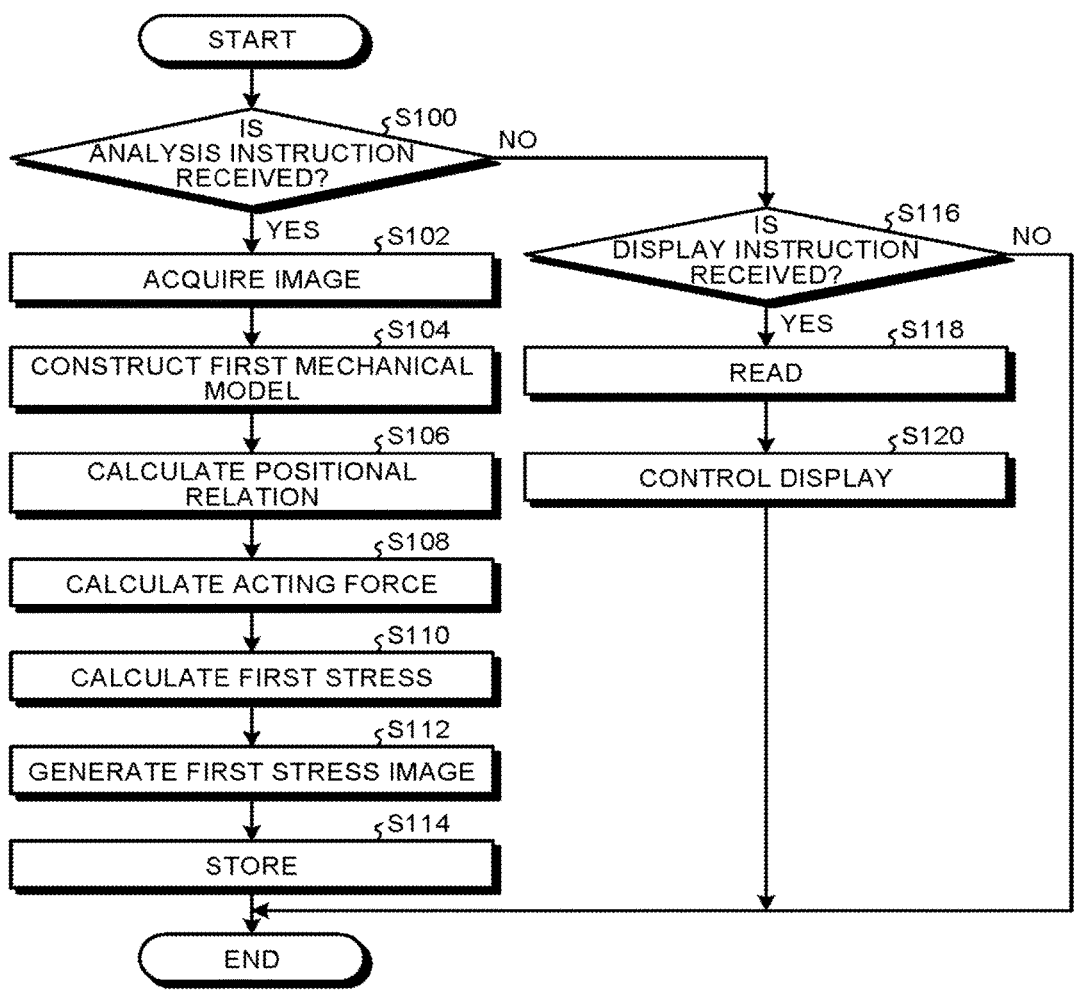
FIG. 7 is a flowchart of a process of an image analysis.

The following describes the process of the image analysis performed by the image analyzing device 10. FIG. 7 is a flowchart of an example of the process of the image analysis performed by the image analyzing device 10.

The receiver 12D determines whether it has received an analysis instruction from the input unit 14A (Step S100). The user, for example, operates the input unit 14A, thereby instructing an image analysis or display of an analysis image. If the receiver 12D receives a signal indicating an image analysis from the input unit 14A, the receiver 12D determines that it has received an analysis instruction (Yes at Step S100).

If the receiver 12D makes an affirmative determination at Step S100 (Yes at Step S100), the first acquirer 12A acquires a CT image (Step S102).

The constructor 12E constructs a first mechanical model from the CT image acquired at Step S102 (Step S104).

The first calculator 12B uses the CT image acquired at Step S102, thereby calculating the positional relation between bones connected to a joint (Step S106).

The second calculator 12C calculates acting force of a muscle acting on the bones connected to the joint based on the positional relation calculated by the first calculator 12B (Step S108).

The third calculator 12F calculates first stress acting on the joint based on the first mechanical model constructed by the constructor 12E at Step S104 and the acting force calculated by the second calculator 12C at Step S108 (Step S110).

The generator 12G generates a first stress image indicating the first stress calculated at Step S110 (Step S112). The generator 12G according to the present embodiment generates an analysis image including the first stress image as described above.

The generator 12G stores the analysis image generated at Step S112 in the storage 16 (Step S114). Subsequently, the present routine is terminated. At Step S114, the generator 12G preferably stores the analysis image generated at Step S112 in the storage 16 in a manner associated with identification information for identifying the analysis image. The identification information preferably includes at least one of the subject ID of the subject in the CT image acquired at Step S102, the date and time of capturing of the CT image, the date and time of generation of the analysis image, and the joint angle of the joint included in the CT image, for example. The first acquirer 12A, for example, acquires the subject ID of the subject in the CT image and the date and time of capturing of the CT image together with the CT image. In this case, the generator 12G uses the subject ID and the data and time of capturing as the identification information. Alternatively, the generator 12G receives the joint angle of the joint in the first stress image included in the analysis image from the second calculator 12C. In this case, the generator 12G uses the received joint angle as the identification information.

By contrast, if the receiver 12D makes a negative determination at Step S100 (No at Step S100), the process proceeds to Step S116. If the receiver 12D receives a signal indicating display of an analysis image from the input unit 14A, for example, the receiver 12D makes a negative determination at Step S100. The receiver 12D then determines whether it has received a display instruction. The receiver 12D, for example, determines whether it has received a display instruction to display an analysis image from the input unit 14A. If the receiver 12D makes an affirmative determination at Step S116 (Yes at Step S116), the process proceeds to Step S118. By contrast, if the receiver 12D makes a negative determination at Step S116 (No at Step S116), the present routine is terminated.

The display controller 12H reads an analysis image stored in the storage 16 (Step S118). The display controller 12H then performs control to display the read analysis image on the display 14B (Step S120). Subsequently, the present routine is terminated.

At Step S118, the display controller 12H may read at least one of a list of analysis images stored in the storage 16 and a list of pieces of identification information corresponding to the respective analysis images and display it on the display 14B. The user operates the input unit 14A, thereby selecting an analysis image to be displayed or identification information corresponding to the analysis image to be displayed. If the receiver 12D receives a signal indicating an analysis image to be displayed or a signal indicating identification information from the input unit 14A, the display controller 12H may read the analysis image corresponding to the received signal indicating an analysis image or the received signal indicating identification information from the storage 16 and display the analysis image on the display 14B.

The process of the image analysis illustrated in FIG. 7 is given by way of example only, and the process of the image analysis performed by the image analyzing device 10 is not limited to the order illustrated in FIG. 7. The image analyzing device 10 may perform the processing at Step S104 after performing the processing at Step S106 and Step S108. Alternatively, the image analyzing device 10 may perform the processing at Step S104 and the processing at Step S106 and Step S108 in parallel.

As described above, the image analyzing device 10 according to the present embodiment includes the first acquirer 12A, the constructor 12E, the first calculator 12B, the second calculator 12C, and the third calculator 12F. The first acquirer 12A acquires an image relating to a joint of a subject and bones connected to the joint. The constructor 12E constructs the three-dimensional shape of the bones and the joint, and relation characteristics between a load and deformation of the bones and the joint from the image. The first calculator 12B calculates the positional relation between the bones connected to the joint. The second calculator 12C calculates acting force of a muscle acting on the bones connected to the joint based on the positional relation. The third calculator 12F calculates first stress acting on the joint based on the three-dimensional shape of the bones and the joint, the relation characteristics between a load and deformation, and the acting force.

As described above, the image analyzing device 10 according to the present embodiment calculates the first stress acting on the joint using the acting force of the muscle acting on the bones connected to the joint and the first mechanical model. Thus, the image analyzing device 10 according to the present embodiment can calculate the stress acting on the joint with the acting force of the muscle taken into consideration.

The image analyzing device 10 according to the present embodiment can accurately calculate the stress acting on the joint of the subject.

The image analyzing device 10 according to the present embodiment includes the first acquirer 12A, the constructor 12E, the first calculator 12B, the second calculator 12C, the third calculator 12F, and the display controller 12H. The first acquirer 12A acquires an image relating to a joint of a subject and bones connected to the joint. The constructor 12E constructs the three-dimensional shape of the bones and the joint, and relation characteristics between a load and deformation of the bones and the joint from the image. The first calculator 12B calculates the positional relation between the bones connected to the joint. The second calculator 12C calculates acting force of a muscle acting on the bones connected to the joint based on the positional relation. The third calculator 12F calculates first stress acting on the joint based on the three-dimensional shape of the bones and the joint, the relation characteristics between a load and deformation, and the acting force. The display controller 12H display a first stress image indicating the first stress on a display.

Second Embodiment

The present embodiment further calculates second stress acting on an artificial joint. The present embodiment models an artificial joint structure.

Figure 8:
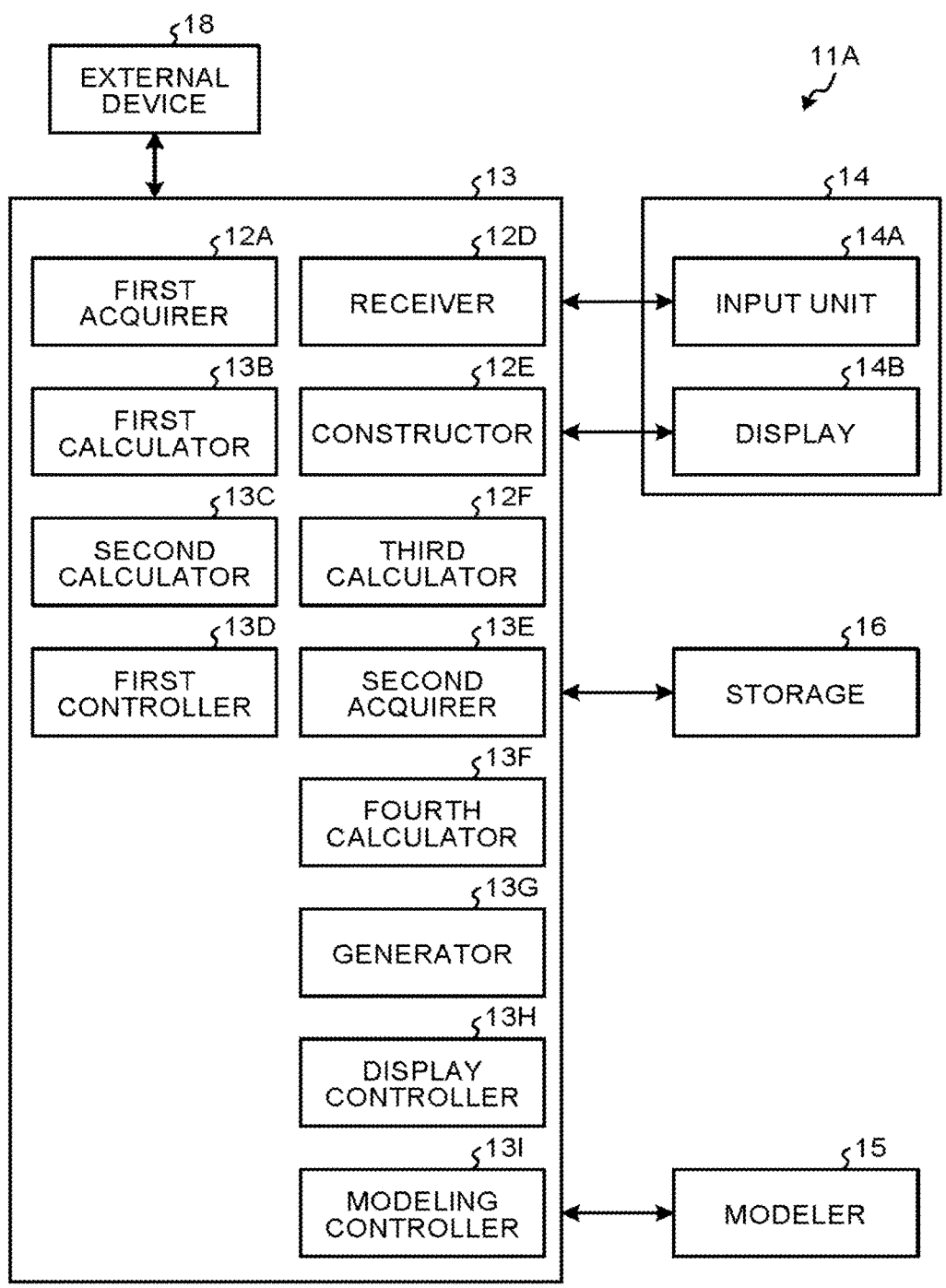
FIG. 8 is a configuration diagram of an image analyzing device.

FIG. 8 is a configuration diagram of an image analyzing device 11A according to the present embodiment. The image analyzing device 11A is connected to the external device 18. The external device 18 is identical to that according to the first embodiment.

The image analyzing device 11A includes a controller 13, the UI 14, the storage 16, and a modeler 15. The UI 14, the storage 16, the modeler 15, and the external device 18 are connected to the controller 13 in a manner transmitting and receiving data and signals thereto and therefrom.

The UI 14 and the storage 16 are identical to those according to the first embodiment.

The modeler 15 is a known device that produces a three-dimensional modeled object. The modeler 15 simply needs to be capable of modeling a three-dimensional modeled object. The modeler 15 may employ a fused deposition modeling system or a binder jetting system, for example.

The material used for modeling by the modeler 15 according to the present embodiment preferably satisfies the range of mechanical characteristics of human bones, joints, and cartilages.

The controller 13 controls the image analyzing device 11A. The controller 13 includes the first acquirer 12A, a first calculator 13B, a second calculator 13C, a first controller 13D, the receiver 12D, the constructor 12E, the third calculator 12F, a second acquirer 13E, a fourth calculator 13F, a generator 13G, a display controller 13H, and a modeling controller 13I.

A part or all of the first acquirer 12A, the first calculator 13B, the second calculator 13C, the first controller 13D, the receiver 12D, the constructor 12E, the third calculator 12F, the second acquirer 13E, the fourth calculator 13F, the generator 13G, the display controller 13H, and the modeling controller 13I may be provided by a processor, such as a CPU, executing a computer program, that is, as software. Alternatively, a part or all of them may be provided as hardware, such as an IC, or a combination of software and hardware.

The first acquirer 12A, the receiver 12D, the constructor 12E, and the third calculator 12F are identical to those according to the first embodiment. The first acquirer 12A, the receiver 12D, the constructor 12E, and the third calculator 12F will be explained in a simplified manner.

The first acquirer 12A acquires an image (a CT image in the present embodiment) relating to a joint of a subject and bones connected to the joint. The first acquirer 12A outputs the acquired CT image to the first calculator 13B and the constructor 12E.

The constructor 12E constructs a first mechanical model from the CT image acquired by the first acquirer 12A.

Similarly to the first calculator 12B according to the first embodiment, the first calculator 13B calculates the positional relation between the bones connected to the joint using the CT image received from the first acquirer 12A, thereby generating a musculoskeletal model. As described above, the positional relation includes an angle (joint angle) formed around the joint by the bones connected to the joint, the bone-centered coordinate system, the moment of inertia, the mass of the bones, and the muscle Jacobian, for example. As described in the first embodiment, standard values of the moment of inertia, the mass of the bones, and the muscle Jacobian may be calculated in advance by the controller 13 and stored in the storage 16. The first calculator 13B may use the moment of inertia, the mass of the bones, and the muscle Jacobian stored in the storage 16.

The first calculator 13B according to the present embodiment extracts a muscle from the CT image acquired by the first acquirer 12A. The first calculator 13B extracts a region having a CT value of a soft tissue (muscle) from the CT image, thereby extracting a muscle region. The first calculator 13B further calculates the feature indicating the length of the muscle based on feature points of the muscle in the extracted muscle region including the start portion and the end portion on the bones.

The first calculator 13B arranges the three-dimensional shape of the muscle on the bone-and-joint shape model indicating the three-dimensional shape of the joint and bones. The first calculator 13B adds the calculated positional relation to the obtained bone-and-joint shape model, thereby generating a musculoskeletal model. The first calculator 13B provides the feature indicating the length of the muscle to the position corresponding to the muscle in the musculoskeletal model.

The second calculator 13C calculates acting force of the muscle acting on the bones connected to the joint based on the positional relation and the feature indicating the length of the muscle calculated by the first calculator 13B.

The second calculator 13C according to the present embodiment calculates at least one of the muscle tension of the muscle coupled to the bones, the torque acting on the joint, and the relation characteristics between a load and deformation of the soft tissue attached to the bones as the acting force. The relation characteristics between a load and deformation of the soft tissue attached to the bones are the hardness of the soft tissue (e.g., a tendon and a cartilage) attached to the bones, for example.

Specifically, similarly to the second calculator 12C according to the first embodiment, the second calculator 13C performs inverse dynamic calculation using the positional relation and the feature calculated by the first calculator 13B, thereby calculating the acting force of the muscle acting on the joint.

Specifically, the second calculator 13C calculates the muscle tension of the muscle coupled to the bones connected to the joint and the torque acting on the joint similarly to the second calculator 12C according to the first embodiment.

The second calculator 13C according to the present embodiment performs inverse dynamic calculation using the feature indicating the length of the muscle, thereby calculating the relation characteristics between a load and deformation of the soft tissue attached to the bones (e.g., the hardness of the tendon and the cartilage). The second calculator 13C may calculate the relation characteristics between a load and deformation of the soft tissue attached to the bones by reading standard hardness (relation characteristics between a load and deformation of the soft tissue attached to the bones) stored in the storage 16 in advance.

As described above, the second calculator 13C performs inverse dynamic calculation based on the positional relation and the feature calculated by the first calculator 13B. Thus, the second calculator 13C calculates the acting force of the muscle acting on the joint (the muscle tension, the torque acting on the joint, and the relation characteristics between a load and deformation of the soft tissue attached to the bones).

The third calculator 12F calculates the first stress acting on the joint based on the first mechanical model constructed by the constructor 12E and the acting force calculated by the second calculator 13C. In other words, the third calculator 12F calculates the first stress of each element (each element in the FEM) on the contact surface between the bones and the joint similarly to the first embodiment.

The second acquirer 13E acquires an artificial joint model. The artificial joint model indicates the three-dimensional shape of an artificial joint and the arrangement position of the artificial joint with respect to the bones. The artificial joint model may further include a parameter of the hardness of the artificial joint, for example.

The second acquirer 13E acquires the artificial joint model from the input unit 14A, for example. The user, for example, operates the input unit 14A, thereby inputting the three-dimensional shape and the arrangement position of the artificial joint. The image analyzing device 11A may generate the three-dimensional shape and the arrangement position of the artificial joint using known image creation software or the like in response to the operation performed by the user on the input unit 14A. The second acquirer 13E acquires the artificial joint model from the input unit 14A. The artificial joint model may be stored in the storage 16 in advance. In this case, the second acquirer 13E may acquire the artificial joint model from the storage 16. The display controller 13H may display a list of artificial joint models stored in the storage 16 on the display 14B. When the user issues an operating instruction via the input unit 14A to select a desired artificial joint model from the displayed list of artificial joint models, the second acquirer 13E may acquire the selected artificial joint model.

Figure 9:
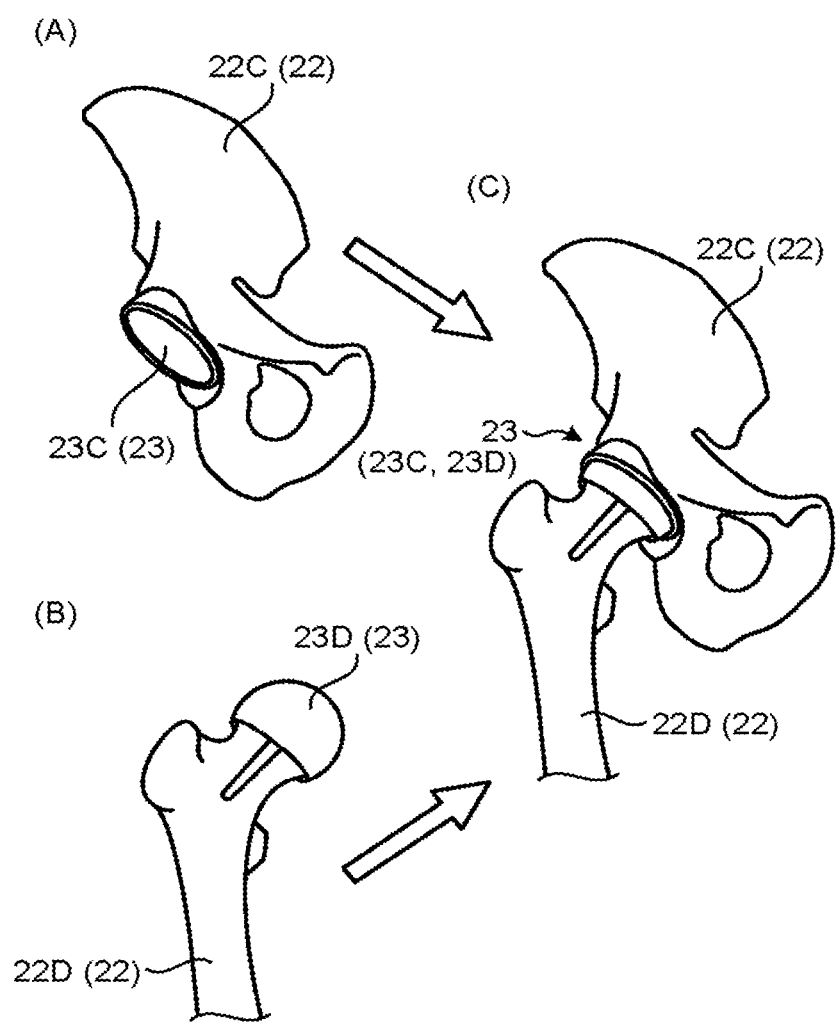
FIG. 9 illustrates an artificial joint model.

FIG. 9 illustrates an example of an artificial joint model 23. The artificial joint model 23 includes the three-dimensional shape of an artificial joint 23C (refer to (A) in FIG. 9) attached to a bone 22C and an artificial joint 23D (refer to (B) in FIG. 9) attached to a bone 22D, for example. The artificial joint 23C and the artificial joint 23D, for example, are arranged at the arrangement position illustrated in (C) in FIG. 9 on the bone 22C and the bone 22D, respectively.

The user operates the input unit 14A, thereby inputting the three-dimensional shape of the artificial joint model 23 and the arrangement position of the artificial joint with respect to the bones 22. Thus, the second acquirer 13E acquires the artificial joint model.

The three-dimensional shape and the arrangement position of the artificial joint in the artificial joint model 23 can be changed as appropriate by an operating instruction issued by the user via the input unit 14A.

Referring back to FIG. 8, the fourth calculator 13F removes the shape model of the joint from the first mechanical model constructed by the constructor 12E. The fourth calculator 13F replaces the shape model of the joint with the artificial joint model acquired by the second acquirer 13E, thereby constructing a second mechanical model. The fourth calculator 13F calculates second stress acting on the artificial joint based on the constructed second mechanical model and the acting force calculated by the second calculator 13C.

Specifically, the fourth calculator 13F removes the shape model indicating the three-dimensional shape of the joint from the bone-and-joint shape model indicating the three-dimensional shape of the bones and the joint included in the first mechanical model. The fourth calculator 13F then arranges the three-dimensional shape of the artificial joint indicated by the artificial joint model at the arrangement position indicated by the artificial joint model in the bone-and-joint shape model from which the shape model of the joint is removed. Thus, the fourth calculator 13F constructs the second mechanical model.

Similarly to the third calculator 12F, the fourth calculator 13F calculates the second stress of each element (each element in the FEM) on the contact surface between the bones and the artificial joint based on the second mechanical model and the acting force calculated by the second calculator 13C.

Let us assume a case where the receiver 12D receives a change instruction to change at least one of the three-dimensional shape and the arrangement position of the artificial joint. In this case, the fourth calculator 13F reconstructs the second mechanical model by adding an artificial joint model indicating at least one of the three-dimensional shape and the arrangement position of the artificial joint changed by the received change instruction to the first mechanical model. In other words, the fourth calculator 13F reconstructs the second mechanical model by changing at least one of the three-dimensional shape and the arrangement position of the artificial joint in response to the change instruction received by the receiver 12D. Similarly to the third calculator 12F, the fourth calculator 13F then calculates the second stress based on the reconstructed second mechanical model and the acting force calculated by the second calculator 13C.

The first controller 13D controls the receiver 12D and the fourth calculator 13F so as to repeatedly perform reception of a change instruction and calculation of the second stress based on the received change instruction in this order until the second stress calculated by the fourth calculator 13F becomes lower than the first stress calculated by the third calculator 12F.

The first controller 13D, for example, repeatedly controls the receiver 12D and the fourth calculator 13F until the second stress calculated for all the elements on the contact surface between the bones and the artificial joint becomes lower than the first stress corresponding to the respective elements. The first controller 13D may repeatedly control the receiver 12D and the fourth calculator 13F until the second stress calculated for at least one of all the elements on the contact surface between the bones and the artificial joint becomes lower than the first stress corresponding to the element.

The state in which the second stress is lower than the first stress means a state in which the use of the artificial joint reduces the stress acting on the joint.

The modeling controller 13I controls modeling performed by the modeler 15. The modeling controller 13I according to the present embodiment controls the modeler 15 so as to model a three-dimensional artificial joint structure corresponding to the artificial joint model included in the second mechanical model used for calculation of the second stress when the second stress is lower than the first stress.

Thus, the modeler 15 models the three-dimensional artificial joint structure with reduced stress acting on the joint under the control of the modeling controller 13I.

When the second stress is lower than the first stress, the modeling controller 13I may control the modeler 15 so as to model both a three-dimensional bone structure of the bones and a three-dimensional artificial joint structure. The three-dimensional bone structure corresponds to the bone-and-joint shape model (not including the three-dimensional shape of the joint) included in the second mechanical model used for calculation of the second stress, whereas the three-dimensional artificial joint structure corresponds to the artificial joint model.

The generator 13G generates an analysis image including the first stress image and a second stress image.

As described in the first embodiment, the first stress image indicates the first stress acting on the joint calculated by the third calculator 12F. In other words, the first stress image indicates a stress region on which the first stress acts on the contact surface between the bones and the joint of the subject with color density corresponding to the intensity of the first stress. Similarly to the first embodiment, the color density indicates at least one of the color and the density.

The second stress image indicates the second stress acting on the artificial joint calculated by the fourth calculator 13F. In other words, the second stress image indicates a stress region on which the second stress acts on the contact surface between the bones of the subject and the artificial joint with color density corresponding to the intensity of the second stress.

The generator 13G preferably generates an image indicating the second stress, which is calculated by the fourth calculator 13F, being lower than the first stress calculated by the third calculator 12F as the second stress image.

The display controller 13H performs control to display an analysis image 51 including the first stress image 30 and a second stress image 52 generated by the generator 13G on the display 14B (refer to FIGS. 10 to 14).

Figure 10:
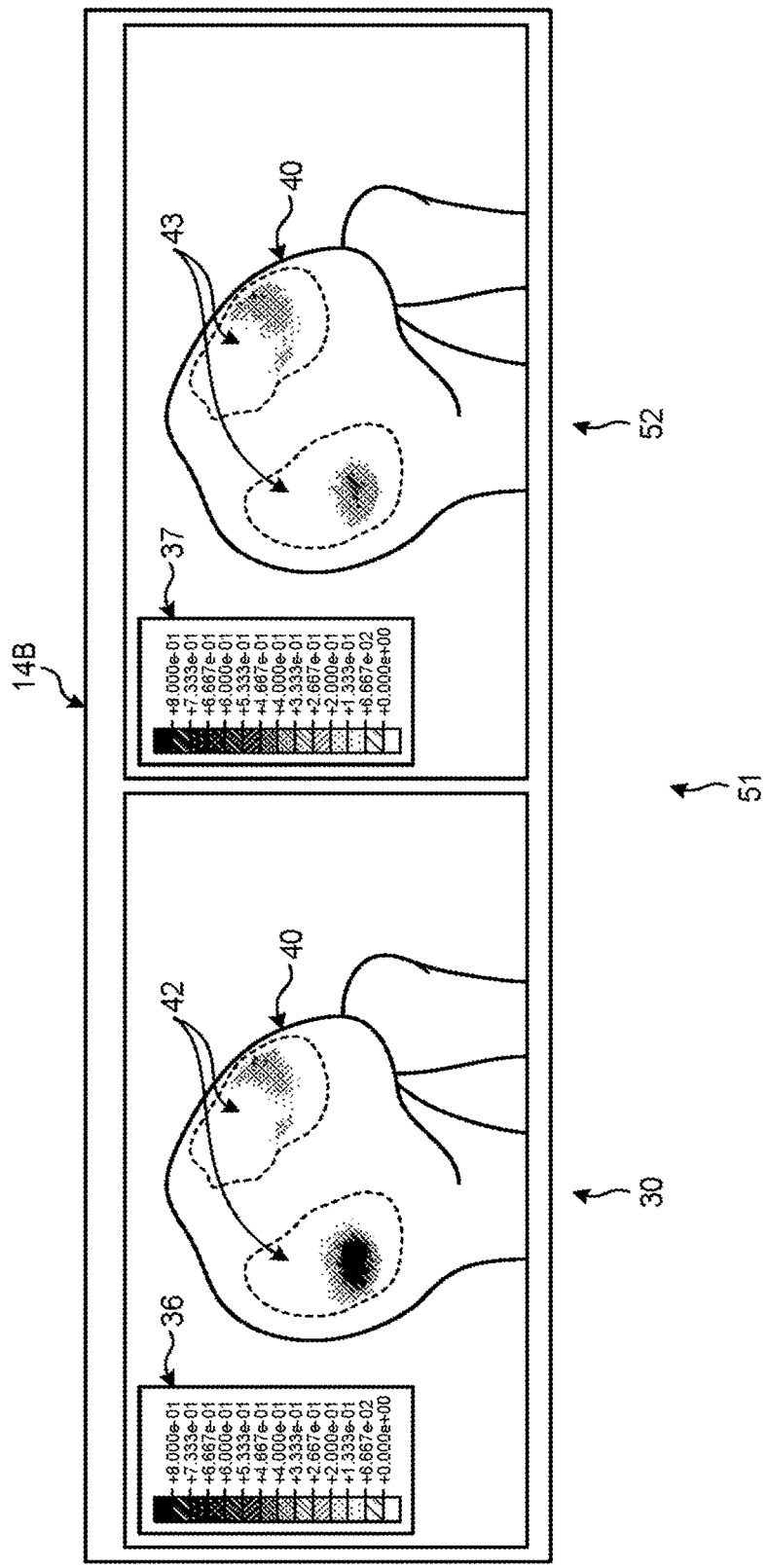
FIG. 10 is a schematic of an analysis image.

FIG. 10 is a schematic of an example of the analysis image 51. The analysis image 51 includes the first stress image 30 and the second stress image 52, for example.

As described in the first embodiment, the first stress image 30 indicates the bone image 40 and the stress region 42 on which the first stress acts on the contact surface between the bones and the joint with the color density corresponding to the intensity of the acting first stress. The first stress image 30 may further include the gauge 36 indicating the color density corresponding to the intensity of the first stress.

The second stress image 52 indicates the bone image 40 and a stress region 43 on which the second stress acts on the contact surface between the bones and the artificial joint with the color density corresponding to the intensity of the acting second stress. The second stress image 52 may further include a gauge 37 indicating the color density corresponding to the intensity of the second stress.

As described above, the image analyzing device 11A displays the analysis image 51 including the first stress image 30 and the second stress image 52 on the display 14B. Thus, the image analyzing device 11A can display the stress acting on the joint before surgery (before insertion of the artificial joint) side by side with the stress acting on the artificial joint after the surgery (after insertion of the artificial joint).

Figure 11:
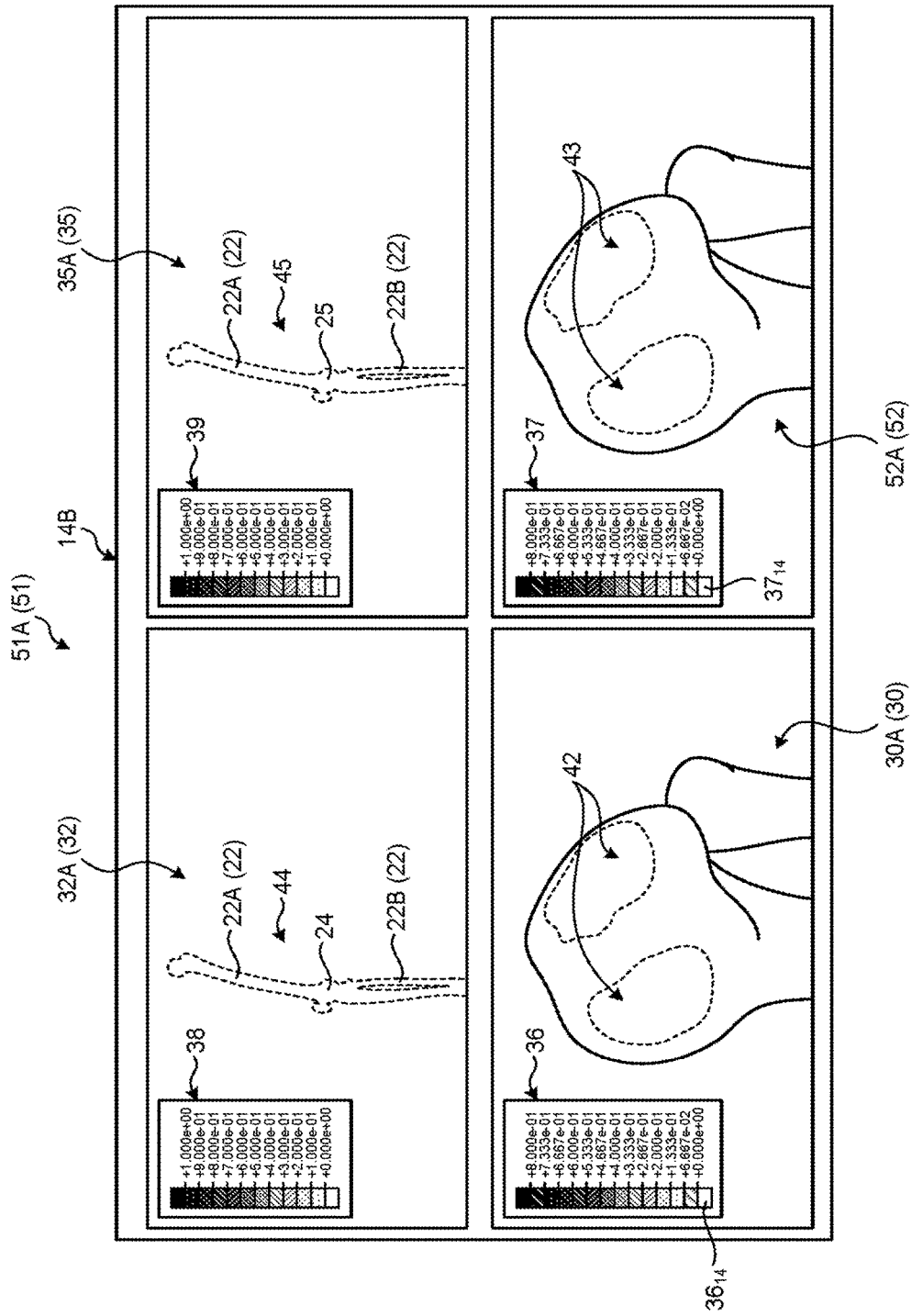
FIG. 11 is a schematic of another analysis image.

FIG. 11 is a schematic of another mode of the analysis image 51. The analysis image 51 may further include at least one of the first mechanical model image 32 indicating the first mechanical model and a second mechanical model image 35 indicating the second mechanical model.

As described in the first embodiment, the first mechanical model image 32 includes the shape model image 44 and the gauge 38.

The shape model image 44 three-dimensionally indicates the positional relation between the bones 22 (22A and 22B) and the joint 24 when the distribution and the intensity of the first stress acting on the contact surface between the bones and the joint are those of the first stress indicated by the first stress image 30 included in the same analysis image 51.

The gauge 38 is an image displaying a list of color densities corresponding to the intensities of the relation characteristics between a load and deformation in a manner associated with the values of the relation characteristics corresponding to the respective color densities. The shape model image 44 is provided with the color density corresponding to the value of the relation characteristics between a load and deformation.

The second mechanical model image 35 includes a shape model image 45 and a gauge 39.

The shape model image 45 three-dimensionally indicates the positional relation between the bones 22 (22A and 22B) and an artificial joint 25 when the distribution and the intensity of the second stress acting on the contact surface between the bones and the artificial joint are those of the second stress indicated by the second stress image 52 included in the same analysis image 51.

The gauge 39 is an image displaying a list of color densities corresponding to the intensities of the relation characteristics between a load and deformation in a manner associated with the values of the relation characteristics corresponding to the respective color densities. The shape model image 45 is provided with the color density corresponding to the value of the relation characteristics between a load and deformation.

The generator 13G generates the analysis image 51 including the first stress image 30, the first mechanical model image 32, the second stress image 52, and the second mechanical model image 35. Thus, the display 14B displays an analysis image 51A illustrated in FIG. 11, for example.

The generator 13G may change the positional relation between the joint 24 and the bones 22 and between the artificial joint 25 and the bones 22, thereby generating the first stress image 30, the first mechanical model image 32, the second stress image 52, and the second mechanical model image 35 corresponding to the change in the positional relation.

The generator 13G, for example, controls the first calculator 13B, the constructor 12E, the second calculator 13C, the third calculator 12F, the second acquirer 13E, the fourth calculator 13F, and the first controller 13D so as to calculate the first stress acting on the joint 24 and the second stress acting on the artificial joint 25 when the positional relations between the joint 24 and the bones 22 and between the artificial joint 25 and the bones 22 change the joint angle from 180° to 45°. The generator 13G acquires the distribution of the first stress corresponding to each joint angle from the third calculator 12F. The generator 13G also acquires the distribution of the second stress corresponding to each joint angle from the fourth calculator 13F.

Let us assume a case where the time-series CT images acquired by the first acquirer 12A are images obtained by changing the joint angle (changing the joint angle from 180° to 45°, for example). In this case, the first calculator 13B, the constructor 12E, the second calculator 13C, the third calculator 12F, the second acquirer 13E, the fourth calculator 13F, and the first controller 13D perform the processing described above using the time-series CT images acquired by the first acquirer 12A, thereby calculating the distribution of the first stress and the distribution of the second stress corresponding to each joint angle. In this case, the generator 13G acquires the distribution of the first stress corresponding to each joint angle from the third calculator 12F and the distribution of the second stress corresponding to each joint angle from the fourth calculator 13F.

The generator 13G generates the first stress image 30 and the second stress image 52 corresponding to each joint angle. The display controller 13H displays the analysis image 51 including the first stress image 30 and the second stress image 52 generated by the generator 13G on the display 14B. The generator 13G may generate the first mechanical model image 32 and the second mechanical model image 35 to generate the analysis image 51 including the first stress image 30, the first mechanical model image 32, the second stress image 52, and the second mechanical model image 35.

Figure 12:
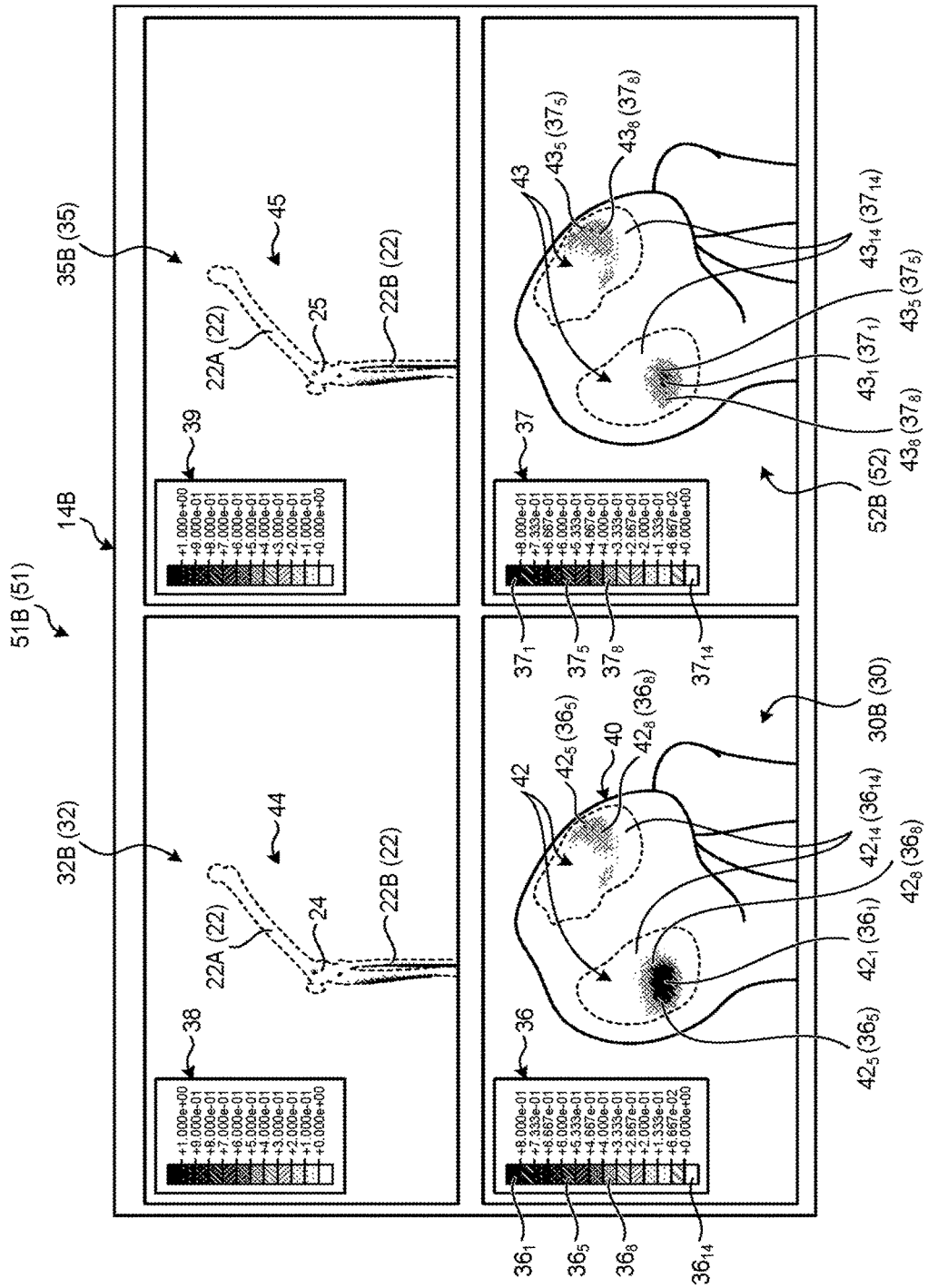
FIG. 12 is a schematic of still another analysis image.
Figure 13:
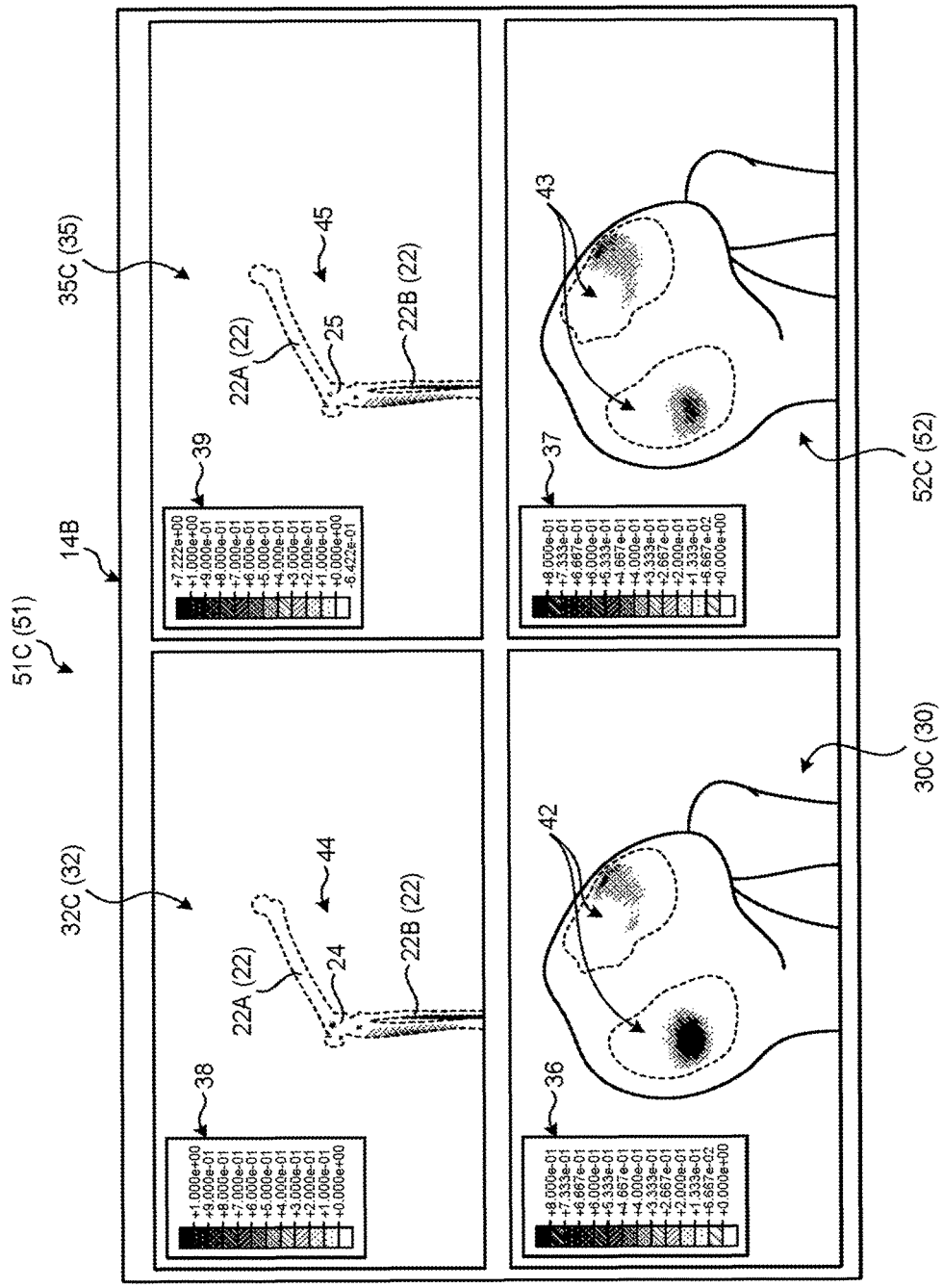
FIG. 13 is a schematic of still another analysis image.

In this case, the display controller 13H displays the analysis image 51 on the display 14B, thereby displaying the analysis images 51 illustrated in FIGS. 11 to 13 on the display 14B, for example.

FIG. 11 is a schematic of an example of the analysis image 51A including the first mechanical model image 32A, the first stress image 30A, a second stress image 52A, and a second mechanical model image 35A when the joint angle is approximately 180°. In the example illustrated in FIG. 11, the stress region 42 is represented by the color density ($36_{14}$) indicating a first stress of "0" in the gauge 36. The stress region 43 is represented by the color density ($37_{14}$) indicating a second stress of "0".

FIG. 12 is a schematic of an example of an analysis image 51B including the first mechanical model image 32B, the first stress image 30B, a second stress image 52B, and a second mechanical model image 35B when the joint angle is approximately 120°.

In the example illustrated in FIG. 12, the stress region $42_1$ on the contact surface between the bones and the joint is represented by the color density $36_1$ indicating a first stress of "$8 \times 10^{-1}$". The stress region $42_5$ is represented by the color density $36_5$ indicating a first stress of "$5.333 \times 10^{-1}$". The stress region $42_8$ is represented by the color density $36_8$ indicating a first stress of "$4.0 \times 10^{-1}$". The stress region $42_{14}$ positioned outermost is represented by the color density $36_{14}$ indicating a first stress of "0".

In the example illustrated in FIG. 12, a stress region $43_1$ on the contact surface between the bones and the artificial joint is represented by a color density $37_1$ indicating a second stress of "$8 \times 10^{-1}$". A stress region $43_5$ is represented by a color density $37_5$ indicating a second stress of "$5.333 \times 10^{-1}$". A stress region $43_8$ is represented by a color density $37_8$ indicating a second stress of "$4.0 \times 10^{-1}$". A stress region $43_{14}$ positioned outermost is represented by a color density $37_{14}$ indicating a second stress of "0".

As illustrated in FIG. 12, the stress region 43 on which the second stress acts in the second stress image 52B has lower intensity of the acting stress and a smaller area on which higher stress acts than the stress region 42 on which the first stress acts in the first stress image 30B. In FIG. 12, the first mechanical model image 32B and the second mechanical model image 35B included in the analysis image 51B indicate that the angle formed by the bone 22A and the bone 22B is approximately 120°.

FIG. 13 is a schematic of an example of an analysis image 51C including the first mechanical model image 32C, the first stress image 30C, a second stress image 52C, and a second mechanical model image 35C when the joint angle is approximately 90°. Similarly to FIG. 12, the stress regions 42 in the example illustrated in FIG. 13 are represented by respective color densities corresponding to the intensities of the acting first stress, and the stress regions 43 are represented by respective color densities corresponding to the intensities of the acting second stress. In comparison with the color density in the stress region 42 and the stress region 43 in FIG. 12, the stress region 42 in FIG. 13 has a larger area of higher first stress, and the stress region 43 in FIG. 13 has a larger area of higher second stress.

In FIG. 13, the first mechanical model image 32C and the second mechanical model image 35C included in the analysis image 51C indicate that the angle formed by the bone 22A and the bone 22B is approximately 90°.

As described above, the generator 13G generates the first stress image 30 (first stress image 30A, 30B, or 30C) and the second stress image 52 (second stress image 52A, 52B, or 52C) depending on the change in the positional relation between the joint 24 and the bones 22. Thus, the image analyzing device 11A can facilitate the user's recognition of the position and the range on which the first stress at each intensity acts on the contact surface between the bones and the joint and of the position and the range on which the second stress at each intensity acts on the contact surface between the bones and the artificial joint.

Similarly to the display controller 12H according to the first embodiment, the display controller 13H may display the first stress image 30 selectively including the stress region 42 of the first stress having intensity specified by the user and the second stress image 52 selectively including the stress region 43 of the second stress having intensity specified by the user on the display 14B.

Similarly to the display controller 12H according to the first embodiment, the display controller 13H may display the first stress image 30 selectively including the stress region 42 of the first stress falling within a range of intensity specified by the user and the second stress image 52 selectively including the stress region 43 of the second stress falling within a range of intensity specified by the user on the display 14B.

Figure 14:
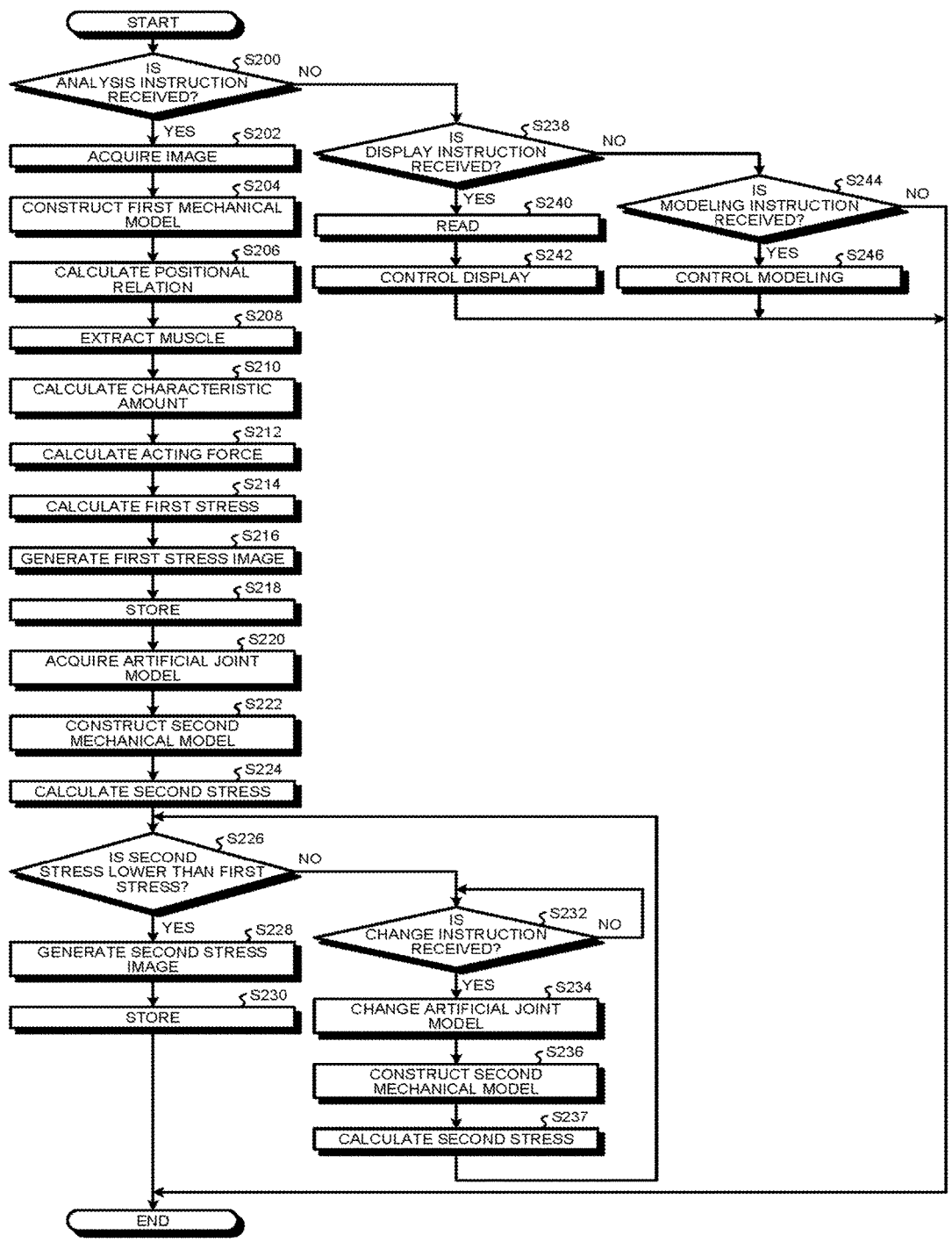
FIG. 14 is a flowchart of a process of an image analysis.

The following describes the process of the image analysis performed by the image analyzing device 11A. FIG. 14 is a flowchart of an example of the process of the image analysis performed by the image analyzing device 11A.

The receiver 12D determines whether it has received an analysis instruction from the input unit 14A (Step S200). The user, for example, operates the input unit 14A, thereby instructing an image analysis, display of an analysis image, or modeling. If the receiver 12D receives a signal indicating an image analysis from the input unit 14A, the receiver 12D determines that it has received an analysis instruction (Yes at Step S200).

If the receiver 12D makes an affirmative determination at Step S200 (Yes at Step S200), the first acquirer 12A acquires a CT image (Step S202).

The constructor 12E constructs a first mechanical model from the CT image acquired at Step S202 (Step S204).

The first calculator 13B uses the CT image acquired at Step S202, thereby calculating the positional relation between a plurality of bones connected to a joint (Step S206).

The first calculator 13B extracts a muscle from the CT image acquired at Step S202 (Step S208). The first calculator 13B calculates the feature indicating the length of the muscle based on feature points of the extracted muscle including the start portion and the end portion on the bones (Step S210). The first calculator 13B arranges the three-dimensional shape of the muscle on the bone-and-joint shape model indicating the three-dimensional shape of the joint and bones and adds the calculated positional relation to the obtained bone-and-joint shape model, thereby generating a musculoskeletal model. The first calculator 13B provides the feature indicating the length of the muscle to the position corresponding to the muscle in the musculoskeletal model.

The second calculator 13C calculates acting force of the muscle acting on the bones connected to the joint based on the positional relation and the feature indicating the length of the muscle calculated by the first calculator 13B (Step S212).

The third calculator 12F calculates first stress acting on the joint based on the first mechanical model constructed by the constructor 12E at Step S204 and the acting force calculated by the second calculator 13C at Step S212 (Step S214).

The generator 13G generates a first stress image indicating the first stress calculated at Step S214 (Step S216). At Step S216, the generator 13G may also generate a first mechanical model image corresponding to the first stress image.

The generator 13G stores the generated first stress image in the storage 16 (Step S218). At Step S218, the generator 13G preferably stores the first stress image generated at Step S216 in the storage 16 in a manner associated with identification information for identifying the first stress image. The identification information preferably includes at least one of the subject ID of the subject in the CT image acquired at Step S202, the date and time of capturing of the CT image, the date and time of generation of the analysis image, and the joint angle of the joint included in the CT image, for example.

The second acquirer 13E acquires an artificial joint model input by an operation performed by the user via the input unit 14A (Step S220).

The fourth calculator 13F removes the shape model of the joint from the first mechanical model constructed by the constructor 12E at Step S204. The fourth calculator 13F replaces the shape model of the joint with the artificial joint model acquired by the second acquirer 13E at Step S220, thereby constructing a second mechanical model (Step S222). The fourth calculator 13F calculates second stress acting on the artificial joint based on the constructed second mechanical model and the acting force calculated by the second calculator 13C at Step S212 (Step S224).

The first controller 13D determines whether the second stress calculated at Step S224 is lower than the first stress calculated at Step S214 (Step S226).

If the second stress is equal to or higher than the first stress (No at Step S226), the process proceeds to Step S232. At Step S232, the first controller 13D repeatedly makes a negative determination until the receiver 12D receives a change instruction to change at least one of the three-dimensional shape and the arrangement position of the artificial joint (No at Step S232). At Step S232, the first controller 13D, for example, controls the display controller 13H, thereby displaying a receiving screen for a change instruction to change at least one of the three-dimensional shape and the arrangement position of the artificial joint on the display 14B. The user, for example, operates the input unit 14A while referring to the receiving screen, thereby inputting a change instruction to change at least one of the three-dimensional shape and the arrangement position of the artificial joint. Thus, the receiver 12D receives the change instruction.

If the first controller 13D makes an affirmative determination at Step S232 (Yes at Step S232), the process proceeds to Step S234. At Step S234, the fourth calculator 13F changes at least one of the three-dimensional shape and the arrangement position of the artificial joint in response to the change instruction received by the receiver 12D at Step S232 (Step S234). The fourth calculator 13F reconstructs the second mechanical model resulting from the change (Step S236). The fourth calculator 13F calculates the second stress based on the second mechanical model reconstructed at Step S236 and the acting force calculated by the second calculator 13C at Step S212 (Step S237). The process is returned to Step S226.

The first controller 13D controls the receiver 12D and the fourth calculator 13F so as to repeatedly perform the processing from Step S226 to Step S237 until the second stress calculated by the fourth calculator 13F becomes lower than the first stress calculated by the third calculator 12F (Yes at Step S226). If the first controller 13D makes an affirmative determination at Step S226 (Yes at Step S226), the process proceeds to Step S228.

At Step S228, the generator 13G generates a second stress image indicating the second stress determined to be lower than the first stress at Step S226 (Step S228). At Step S228, the generator 13G may also generate a second mechanical model image corresponding to the second stress image.

The generator 13G stores the generated second stress image in the storage 16 (Step S230). Subsequently, the present routine is terminated. At Step S230, the generator 13G preferably stores the second stress image generated at Step S228 in the storage 16 in a manner associated with the identification information used for storing of the first stress image at Step S218.

By contrast, if the receiver 12D makes a negative determination at Step S200 (No at Step S200), the process proceeds to Step S238. At Step S238, the receiver 12D determines whether it has received a signal indicating a display instruction to display an analysis image from the input unit 14A.

If the receiver 12D determines that it has received a signal indicating a display instruction to display an analysis image (Yes at Step S238), the process proceeds to Step S240.

At Step S240, the display controller 13H reads an analysis image stored in the storage 16 (Step S240). The display controller 13H performs control to display the read analysis image (including the first stress image 30 and the second stress image 52) on the display 14B (Step S242). Subsequently, the present routine is terminated.

By contrast, the receiver 12D makes a negative determination at Step S238 (No at Step S238), the process proceeds to Step S244. At Step S244, the receiver 12D determines whether it has received a modeling instruction from the input unit 14A. If the receiver 12D determines that it has received a modeling instruction (Yes at Step S244), the process proceeds to Step S246.

At Step S246, the modeling controller 13I controls the modeler 15 so as to model a three-dimensional artificial joint structure corresponding to the artificial joint model included in the second mechanical model used for calculation of the second stress when the second stress is lower than the first stress (Step S246). Subsequently, the present routine is terminated. Thus, the modeler 15 models the three-dimensional artificial joint structure with reduced stress acting on the joint under the control of the modeling controller 13I.

At Step S246, the display controller 13H may display a list of the second stress images stored in the storage 16 on the display 14B. When the user operates the input unit 14A to select a desired second stress image, the modeling controller 13I may control the modeler 15 so as to model an artificial joint structure corresponding to the artificial joint model included in the second mechanical model used for calculation of the second stress indicated by the selected second stress image.

If the receiver 12D makes a negative determination at Step S244 (No at Step S244), the present routine is terminated.

As described above, the image analyzing device 11A according to the present embodiment includes the first acquirer 12A, the constructor 12E, the first calculator 13B, the second calculator 13C, the third calculator 12F, the second acquirer 13E, and the fourth calculator 13F.

The first acquirer 12A acquires an image relating to a joint of a subject and bones connected to the joint. The constructor 12E constructs a first mechanical model indicating the three-dimensional shape of the bones and the joint, and relation characteristics between a load and deformation of the bones and the joint from the image. The first calculator 13B calculates the positional relation between the bones connected to the joint. The second calculator 13C calculates acting force of a muscle acting on the bones connected to the joint based on the positional relation. The third calculator 12F calculates first stress acting on the joint based on the first mechanical model and the acting force. The second acquirer 13E acquires an artificial joint model indicating the three-dimensional shape and the arrangement position of an artificial joint. The fourth calculator 13F calculates second stress acting on the artificial joint based on a second mechanical model obtained by adding the artificial joint model to the first mechanical model and based on the acting force.

As described above, the image analyzing device 11A according to the present embodiment calculates the first stress acting on the joint using the acting force of the muscle acting on the bones connected to the joint and the first mechanical model similarly to the first embodiment. Thus, the image analyzing device 11A according to the present embodiment can calculate the stress acting on the joint with the acting force of the muscle taken into consideration.

The image analyzing device 11A according to the present embodiment further calculates the second stress acting on the artificial joint based on the acting force and the artificial joint model.

The image analyzing device 11A according to the present embodiment can accurately calculate the stress acting on the joint of the subject and the stress before and after the arrangement of the artificial joint (the first stress and the second stress). Thus, the image analyzing device 11A according to the present embodiment is suitably used for simulation performed before surgery to arrange the artificial joint, for example.

Third Embodiment

The present embodiment acquires an image obtained by capturing a site including a joint to be analyzed in a subject in a first load state with a load applied thereto and an image obtained by capturing the site in a second load state with a load smaller than that in the first load state applied thereto.

The first load state is a state in which a predetermined load is applied to the site including the joint to be analyzed in the subject. The second load state is a state in which a load smaller than that in the first load state is applied to the site including the joint to be analyzed in the subject.

The load applied in the first load state is not limited to one type of load and may be a plurality of types of loads having different values. Similarly to this, the load applied in the second load state is not limited to one type of load and may be a plurality of types of loads having different values. The second load state includes a state in which no load is applied (that is, a state in which a load of "0" is applied).

Figure 15:
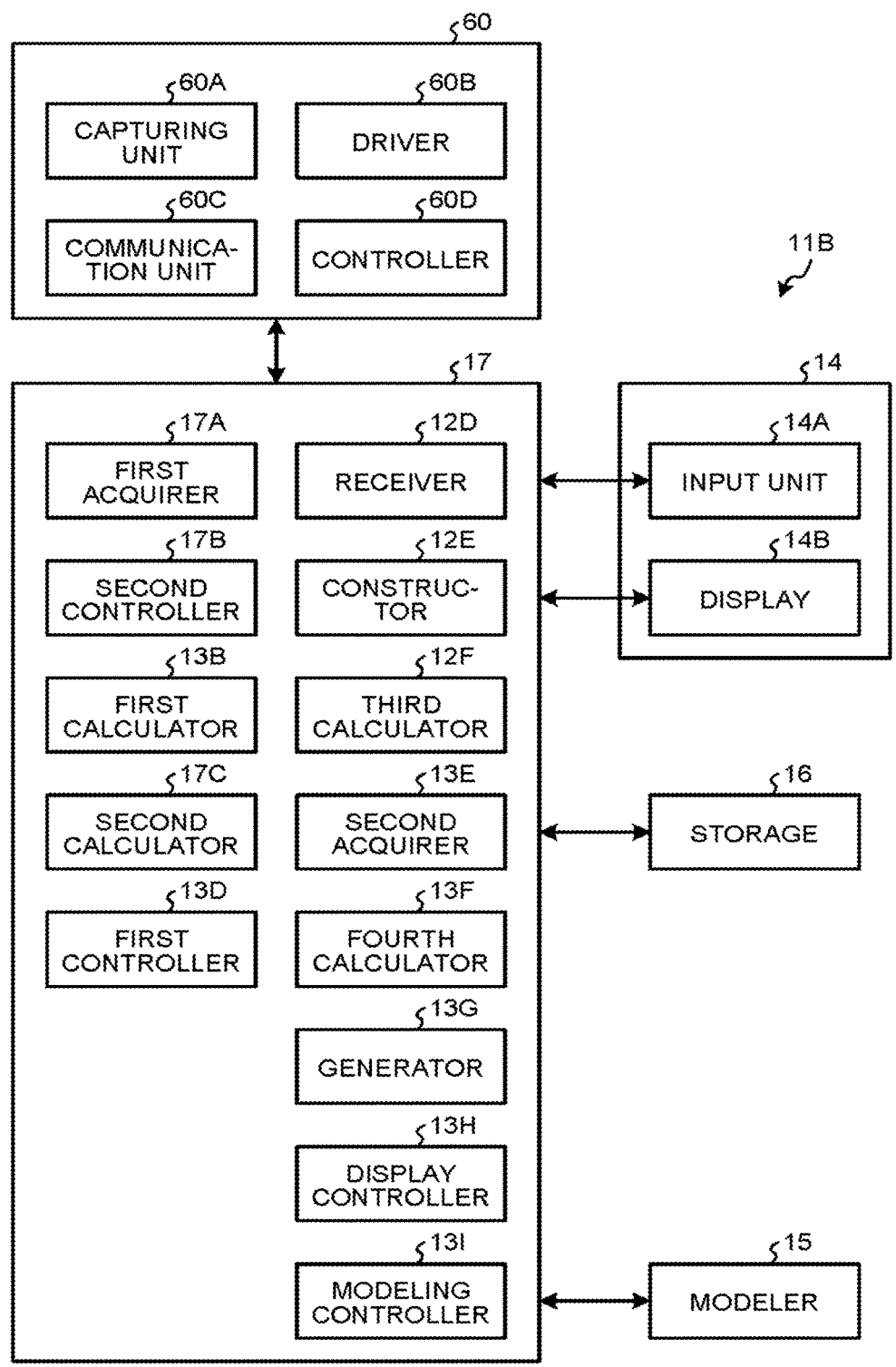
FIG. 15 is a configuration diagram of an image analyzing device.

FIG. 15 is a configuration diagram of an image analyzing device 11B according to the present embodiment. The image analyzing device 11B is connected to an external device 60. The external device 60 captures the subject to provide an image to be analyzed by the image analyzing device 11B. The image analyzing device 11B may include the external device 60.

Figure 16:
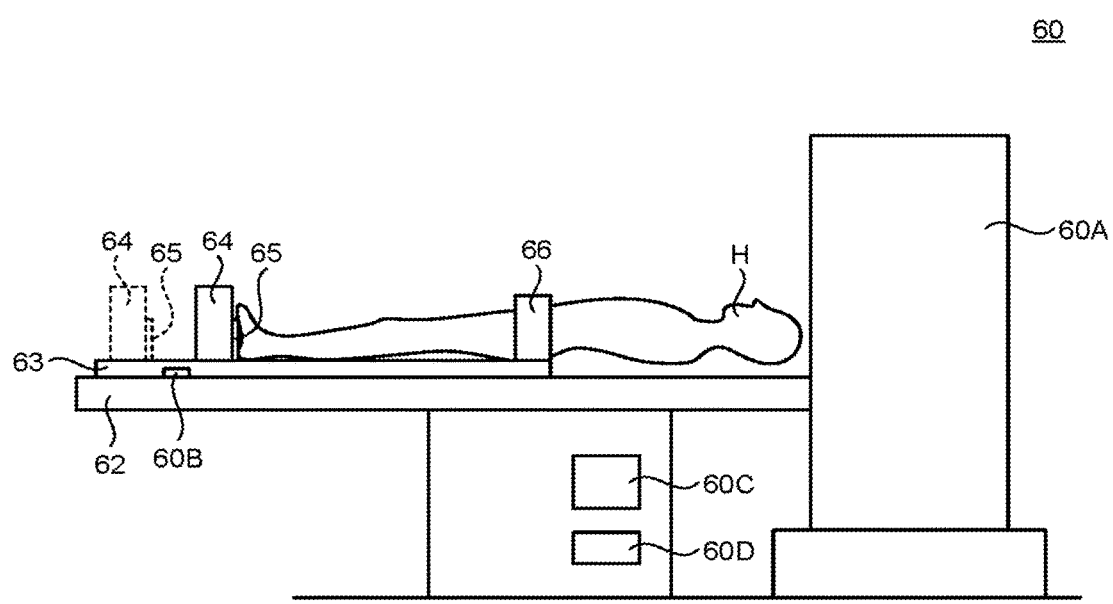
FIG. 16 is a schematic of an external device.

FIG. 16 is a schematic of an example of the external device 60. The external device 60 includes a capturing unit 60A, a support 62, a driver 60B, a communication unit 60C, a controller 60D, a fixing unit 66, a load applying unit 64, a pressure sensor 65, and a guiding member 63. The controller 60D controls the external device 60. The controller 60D is connected to the capturing unit 60A, the driver 60B, the communication unit 60C, and the pressure sensor 65 in a manner transmitting and receiving data and signals thereto and therefrom.

The support 62 is a couch that supports a subject H. The support 62 is provided with the guiding member 63 extending along the longitudinal direction of the support 62. The guiding member 63 is provided with the driver 60B and the load applying unit 64. The load applying unit 64 can be moved along the longitudinal direction of the guiding member 63. The driver 60B reciprocates the load applying unit 64 in the longitudinal direction of the guiding member 63. The fixing unit 66 is fixed to the support 62.

Let us assume a case where the subject H lies on the support 62, for example. The fixing unit 66 is fixed to the waist of the subject H, for example. When the load applying unit 64 is moved along the guiding member 63 in a direction closer to the fixing unit 66 under the control of the controller 60D, a load is applied to the subject H. The load applied to the subject H is detected by the pressure sensor 65. When the load applying unit 64 is moved along the guiding member 63 in a direction away from the fixing unit 66 under the control of the controller 60D, the subject H is released from the loaded state. The positions of the subject H, the fixing unit 66, and the load applying unit 64 are adjusted in advance such that the site including a region to be analyzed (e.g., the knee) in the subject H is positioned between the fixing unit 66 and the load applying unit 64.

The capturing unit 60A provides a CT image or an MR image. The capturing unit 60A can be moved in the longitudinal direction of the support 62 by a driving mechanism, which is not illustrated. Thus, the capturing unit 60A can provide an image obtained by capturing the region to be analyzed in the subject H in the first load state with a load applied to at least the region and an image obtained by capturing the region in the second load state with a load applied to at least the region under the control of the controller 60D.

The communication unit 60C communicates with a controller 17 of the image analyzing device 11B. The communication unit 60C transmits an image (e.g., a CT image) obtained by the capturing unit 60A to the image analyzing device 11B.

Referring back to FIG. 15, the image analyzing device 11B includes the controller 17, the UI 14, the storage 16, and the modeler 15. The UI 14, the storage 16, the modeler 15, and the external device 60 are connected to the controller 17 in a manner transmitting and receiving data and signals thereto and therefrom.

The UI 14, the storage 16, and the modeler 15 are identical to those according to the second embodiment.

The controller 17 controls the image analyzing device 11B. The controller 17 includes a first acquirer 17A, a second controller 17B, the first calculator 13B, a second calculator 17C, the first controller 13D, the receiver 12D, the constructor 12E, the third calculator 12F, the second acquirer 13E, the fourth calculator 13F, the generator 13G, the display controller 13H, and the modeling controller 13I.

A part or all of the first acquirer 17A, the second controller 17B, the first calculator 13B, the second calculator 17C, the first controller 13D, the receiver 12D, the constructor 12E, the third calculator 12F, the second acquirer 13E, the fourth calculator 13F, the generator 13G, the display controller 13H, and the modeling controller 13I may be provided by a processor, such as a CPU, executing a computer program, that is, as software. Alternatively, a part or all of them may be provided as hardware, such as an IC, or a combination of software and hardware.

The first calculator 13B, the first controller 13D, the receiver 12D, the constructor 12E, the third calculator 12F, the second acquirer 13E, the fourth calculator 13F, the generator 13G, the display controller 13H, and the modeling controller 13I are identical to those according to the second embodiment.

The first acquirer 17A acquires an image (a CT image in the present embodiment) relating to a joint of a subject and bones connected to the joint. The first acquirer 17A according to the present embodiment acquires a CT image (referred to as a first image) obtained by capturing a site including the joint to be analyzed in the subject in the second load state and a CT image (referred to as a second image) obtained by capturing the site in the first load state from the external device 60.

The following describes an example in which the second load state is a state with no load applied. As described above, the second load state simply needs to be a state with a load smaller than that in the first load state applied and is not limited to this example.

The second controller 17B controls the external device 60 so as to provide the first image obtained by capturing the site including the joint to be analyzed in the subject in a state with no load applied thereto (second load state) and the second image obtained by capturing the site in a state with a load applied thereto (first load state). The second controller 17B may adjust the magnitude of the load, thereby controlling the external device 60 so as to provide a plurality of first images and a plurality of second images, obtained by capturing the site in a plurality of second load states and obtained by capturing the site in states with a plurality of types of loads applied (a plurality of first load states).

When receiving a capturing instruction from the second controller 17B, the controller 60D of the external device 60 controls the driver 60B and the capturing unit 60A so as to perform capturing in a state in which no load is applied to the subject H (second load state). Thus, the controller 60D obtains the first image. The controller 60D also controls the driver 60B and the capturing unit 60A so as to perform capturing in a state in which a load is applied to the subject H (first load state), thereby obtaining the second image.

The state in which a load is applied is a state in which the pressing sensor 65 detects a predetermined pressure (load), for example. The controller 60D controls the driver 60B so as to move the load applying unit 64 in a direction closer to the fixing unit 66 until the pressure sensor 65 detects the pressure. When the pressure is detected, the controller 60D controls the capturing unit 60A so as to perform capturing. The controller 60D may also control a range of motion of the joint besides the load applied to the joint. The controller 60D may detect the load using a device that can directly measure a load (e.g., a load cell) besides the pressure sensor.

The controller 60D uses the obtained image as the second image. The controller 60D controls the driver 60B so as to move the load applying unit 64 in a direction away from the fixing unit 66 until the pressure detected by the pressure sensor 65 becomes "0". When a pressure of "0" is detected, the controller 60D controls the capturing unit 60A so as to perform capturing. The controller 60D uses the obtained image as the first image. The communication unit 60C transmits the obtained first image and the obtained second image to the image analyzing device 11B. Thus, the first acquirer 17A acquires the first image and the second image.

The first calculator 13B, the first controller 13D, the receiver 12D, the constructor 12E, the third calculator 12F, the second acquirer 13E, the fourth calculator 13F, the generator 13G, the display controller 13H, and the modeling controller 13I perform the same processing as that in the second embodiment using the first image (image obtained by the capturing in the second load state with no load applied) as the CT image.

The second calculator 17C calculates acting force of a muscle acting on the bones connected to the joint using the positional relation and the feature indicating the length of the muscle calculated by the first calculator 13B and the pressure acquired by the pressure sensor 65 (that is, the load applied in the capturing).

The second calculator 17C according to the present embodiment calculates at least one of the muscle tension of the muscle coupled to the bones, the torque acting on the joint, and the relation characteristics between a load and deformation of the soft tissue attached to the bones as the acting force. The relation characteristics between a load and deformation of the soft tissue attached to the bones are the hardness of the soft tissue (e.g., a tendon and a cartilage) attached to the bones, for example.

Specifically, similarly to the second calculator 12C according to the first embodiment, the second calculator 17C performs inverse dynamic calculation using the positional relation and the feature calculated by the first calculator 13B, thereby calculating the acting force of the muscle acting on the joint.

The second calculator 13C according to the second embodiment may calculate the relation characteristics between a load and deformation of the soft tissue attached to the bones (e.g., the hardness of the tendon and the cartilage) by reading standard hardness (relation characteristics between a load and deformation of the soft tissue attached to the bones) stored in the storage 16 in advance.

By contrast, the second calculator 17C according to the present embodiment calculates the relation characteristics between a load and deformation of the soft tissue attached to the bones using the first image and the second image acquired by the first acquirer 17A.

The second calculator 17C, for example, performs a known calculation using the length of the soft tissue extracted from the first image, the length of the soft tissue extracted from the second image, and the load applied by the external device 60 in the capturing of the second image. Thus, the second calculator 17C calculates the relation characteristics between a load and deformation of the soft tissue attached to the bones.

Let us assume a case where the first acquirer 17A acquires a plurality of second images obtained by performing capturing with different loads applied. In this case, the second calculator 17C performs the known calculation using the length of the soft tissue extracted from the first image, the lengths of the soft tissue extracted from the respective second images, and the loads applied by the external device 60 in the capturing of the respective second images. Thus, the second calculator 17C calculates the relation characteristics between a load and deformation of the soft tissue attached to the bones.

Figure 17:
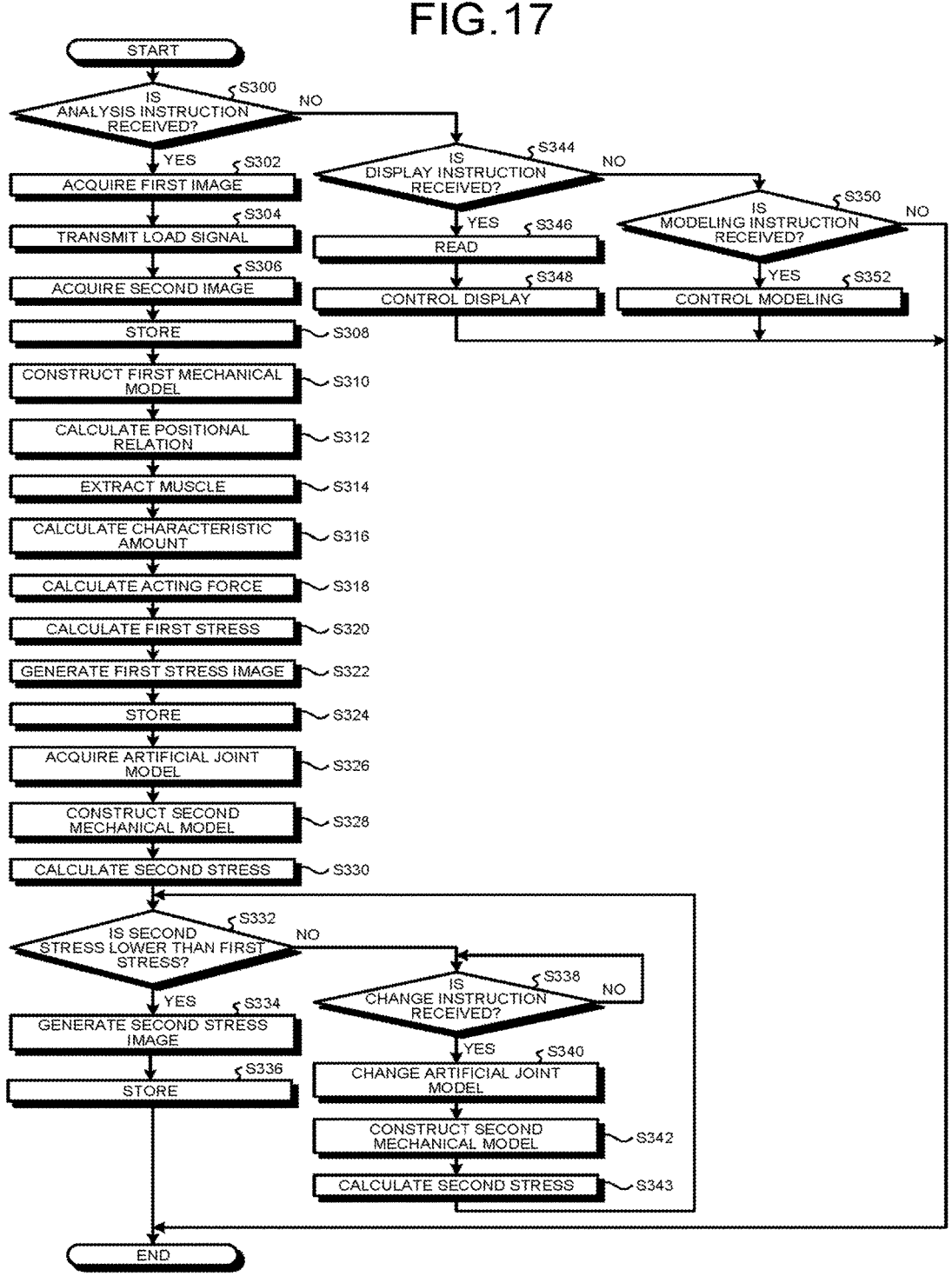
FIG. 17 is a flowchart of a process of an image analysis.

The following describes the process of the image analysis performed by the image analyzing device 11B. FIG. 17 is a flowchart of an example of the process of the image analysis performed by the image analyzing device 11B.

The receiver 12D determines whether it has received an analysis instruction from the input unit 14A (Step S300). The processing at Step S300 is the same as that at Step S200 (refer to FIG. 14).

If the receiver 12D makes an affirmative determination at Step S300 (Yes at Step S300), the first acquirer 17A acquires a first image from the external device 60 (Step S302).

The second controller 17B transmits, to the external device 60, a load signal for instructing the external device 60 to obtain a second image by applying a load (Step S304). The external device 60 that receives the load signal captures a site including a joint to be analyzed in a subject in a first load state with a load of a predetermined pressure applied thereto under the control of the controller 60D. Thus, the external device 60 obtains the second image.

The first acquirer 17A acquires the second image from the external device 60 (Step S306). The first acquirer 17A stores the first image acquired at Step S302 and the second image acquired at Step S306 in the storage 16 (Step S308).

The controller 17 performs processing from Step S310 to Step S352 in the same manner as in the processing from Step S204 to Step S246 in the second embodiment except that the first image acquired at Step S302 is used instead of the CT image used in the second embodiment. Subsequently, the present routine is terminated.

The relation characteristics between a load and deformation of the soft tissue attached to the bones may possibly greatly vary depending on the subject.

The image analyzing device 11B according to the present embodiment calculates the relation characteristics between a load and deformation of the soft tissue attached to the bones using the first image and the second image. The first image is obtained by capturing the site including the object to be analyzed in the subject in the second load state with a load smaller than that in the first load state applied thereto, and the second image is obtained by capturing the site in the first load state with a load applied thereto. Subsequently, the image analyzing device 11B performs the same processing as that in the second embodiment.

Thus, the image analyzing device 11B according to the present embodiment can calculate the first stress acting on the joint of the subject more accurately than in the embodiments above.

Fourth Embodiment

Figure 18:
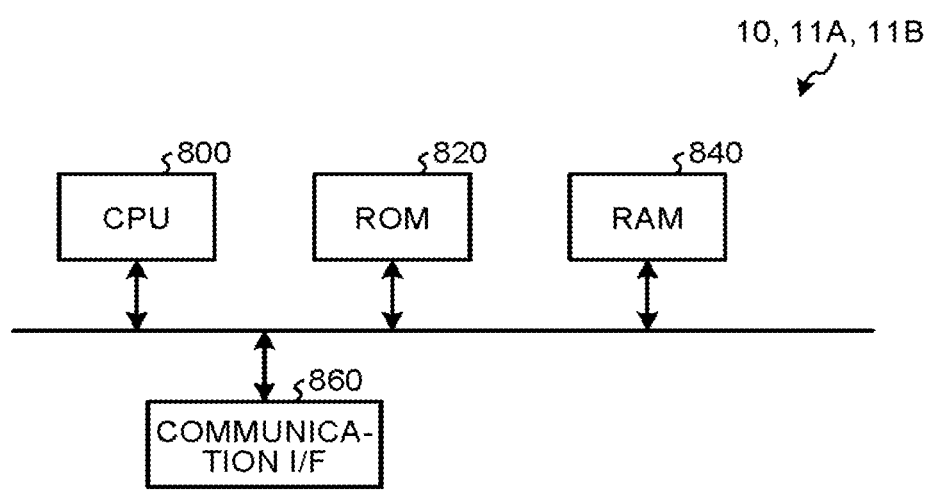
FIG. 18 is a diagram of a hardware configuration of the image analyzing device.

The following describes a hardware configuration of the image analyzing devices 10, 11A, and 11B according to the embodiments above. FIG. 18 is a block diagram of an exemplary hardware configuration of the image analyzing devices 10, 11A, and 11B according to the embodiments above.

The image analyzing devices 10, 11A, and 11B according to the embodiments above each include a CPU 800, a read only memory (ROM) 820, a random access memory (RAM) 840, a hard disk drive (HDD) (not illustrated), and a communication I/F 860. The CPU 800, the ROM 820, the RAM 840, the HDD (not illustrated), and the communication I/F 860 are connected to one another via a bus. The image analyzing devices 10, 11A, and 11B have a hardware configuration of a typical computer.

The computer program for performing the image analysis executed by the image analyzing devices 10, 11A, and 11B according to the embodiments above is embedded and provided in the ROM 820, for example.

The computer program for performing the image analysis executed by the image analyzing devices 10, 11A, and 11B according to the embodiments above may be stored and provided in a computer-readable storage medium, which may be provided as a computer program product, such as a compact disc read only memory (CD-ROM), a floppy (registered trademark) disk (FD), a compact disc recordable (CD-R), and a digital versatile disc (DVD), as an installable or executable file.

The computer program for performing the image analysis executed by the image analyzing devices 10, 11A, and 11B according to the embodiments above may be stored in a computer connected to a network, such as the Internet, and provided by being downloaded via the network. Furthermore, the computer program for performing the image analysis executed by the image analyzing devices 10, 11A, and 11B according to the embodiments above may be provided or distributed via a network, such as the Internet.

The computer program for performing the image analysis executed by the image analyzing devices 10, 11A, and 11B according to the embodiments above has a module configuration including each functional unit described above. In actual hardware, the CPU 800 reads and executes the computer program from a storage medium, such as the ROM 820, to load each functional unit on the main memory. Thus, each functional unit is generated on the main memory.

Modifications

The third calculator 12F of the image analyzing devices 10, 11A, and 11B according to the embodiments above calculates the first stress acting on the joint based on the first mechanical model and the acting force. The third calculator 12F may calculate first pressure acting on the joint instead of or besides the first stress. To calculate the first pressure, the third calculator 12F performs calculation in the same manner as in the calculation of the first stress.

The fourth calculator 13F of the image analyzing devices 11A and 11B according to the embodiments above calculates the second stress acting on the artificial joint based on the second mechanical model and the acting force. The fourth calculator 13F may calculate second pressure acting on the artificial joint instead of or besides the second stress. To calculate the second pressure, the fourth calculator 13F performs calculation in the same manner as in the calculation of the second stress.

The image analyzing devices 10, 11A, and 11B according to the embodiments above are applicable to any type of image analyzing device including a capturing mechanism that captures a subject. The image analyzing devices 10, 11A, and 11B according to the embodiments above are applicable as appropriate to X-ray computed tomography apparatuses (X-ray CT apparatuses), magnetic resonance diagnostic apparatuses, ultrasonic diagnostic apparatuses, single photon emission CT (SPECT) apparatuses, positron emission tomography (PET) apparatuses, and radiotherapy apparatuses, for example.

While the subject according to the embodiments above is assumed to be a human body, it may be an object other than a human body. The subject may be shoes, for example. In this case, the joint in the object corresponds to a part positioned between two parts having stiffness of equal to or higher than a threshold in the object. The bones connected to the joint correspond to parts connected to the part corresponding to the joint and having stiffness of equal to or higher than the threshold. The acting force of the muscle acting on the bones connected to the joint corresponds to acting force of an object other than the parts corresponding to the bones (e.g., a reinforcing member) acting on the parts corresponding to the bones connected to the part corresponding to the joint.

Thus, the image analyzing devices 10, 11A, and 11B according to the embodiments above are also applicable to a case where an object other than a human body is used as the subject.

As described above, the image analyzing devices 10, 11A, and 11B according to the embodiments above include the constructor 12E, the second calculators 12C and 13C, the third calculator 12F, and the display controllers 12H and 13H (refer to FIGS. 1, 8, and 15). The constructor 12E constructs the first mechanical model indicating the three-dimensional shape of the bones and the joint and the relation characteristics between a load and deformation from the image. The second calculators 12C and 13C calculate the acting force of the muscle acting on the bones from the positional relation between the bones. The third calculator 12F calculates the first stress acting on the joint based on the first mechanical model and the acting force. The display controller 13H displays the first stress image indicating the first stress on the display 14B.

Thus, the image analyzing devices 10, 11A, and 11B according to the embodiments above can provide an advantageous effect of facilitating the user's recognition of the intensity of the first stress and the position and the range on which the first stress acts on the contact surface between the bones and the joint besides the advantageous effects of the embodiments above.

According to an embodiment, it is possible to accurately calculate stress acting on a joint.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image analyzing device, comprising:
   processing circuitry configured to
     construct a three-dimensional shape of bones and a joint and relation characteristics between a load and deformation from an image;
     calculate acting force of a muscle acting on the bones based on a positional relation between the bones;
     calculate first stress acting on the joint based on the three-dimensional shape, the relation characteristics, and the acting force; and
     cause a display to display a first stress image indicating the first stress on a display, wherein
   the processing circuitry is further configured to cause the display to display the first stress image indicating a bone image of a bone and a stress region where the first stress acts on a contact surface between the bone and the joint, the first stress image being indicated with a color density corresponding to an intensity of the acting first stress.

2. The device according to claim 1, wherein
   the processing circuitry is further configured to cause the display to display the first stress image including the bone image, the stress region, and a first gauge indicating the color density corresponding to the intensity of the acting first stress.

3. The device according to claim 2, wherein
   the displayed first gauge is an image where a list of color densities corresponding to intensities of the first stress in a manner associated with values of the first stress corresponding to the color densities respectively.

4. The device according to claim 1, wherein
   the processing circuitry is further configured to cause the display to display an analysis image including the first stress image and a shape model image three-dimensionally indicating a positional relation between the bones and the joint.

5. The device according to claim 4, wherein
   the displayed shape model image three-dimensionally indicates the positional relation between the bones and the joint corresponding to a distribution and the intensity of the first stress indicated by the first stress image included in the same analysis image containing the shape model image.

6. The device according to claim 4, wherein
   the processing circuitry is further configured to cause the display to display the analysis image including the first stress image and the shape model image provided with a color density corresponding to a value of the relation characteristics between the load and the deformation.

7. The device according to claim 6, wherein
   the processing circuitry is further configured to cause the display to display the analysis image including the first stress image and a first mechanical model image including the shape model image, wherein
   the first mechanical model image includes a second gauge displaying a list of color densities corresponding to the intensities of the relation characteristics between the load and the deformation in a manner associated with values of the relation characteristics corresponding to the respective color densities.

8. The device according to claim 1, wherein the processing circuitry is further configured to
   generate the first stress image, wherein the first stress image is generated in accordance with a change in a positional relation between the joint and the bones.

9. An image analyzing method, comprising:
   constructing a three-dimensional shape of bones and a joint and relation characteristics between a load and deformation from an image;
   calculating acting force of a muscle acting on the bones based on a positional relation between the bones;
   calculating first stress acting on the joint based on the three-dimensional shape, the relation characteristics, and the acting force; and
   displaying a first stress image indicating the first stress on a display, wherein
   the displaying step including displaying, on the display, the first stress image indicating a bone image of a bone and a stress region where the first stress acts on a contact surface between the bone and the joint, the first stress image being indicated with a color density corresponding to an intensity of the acting first stress.

10. A computer program product comprising a non-transitory computer-readable medium containing a program executed by a computer, the program causing the computer to execute:

constructing a three-dimensional shape of bones and a joint and relation characteristics between a load and deformation from an image;
calculating acting force of a muscle acting on the bones based on a positional relation between the bones;
calculating first stress acting on the joint based on the three-dimensional shape, the relation characteristics, and the acting force; and
displaying a first stress image indicating the first stress on a display, wherein
the displaying step including displaying, on the display, the first stress image indicating a bone image of a bone and a stress region where the first stress acts on a contact surface between the bone and the joint, the first stress image being indicated with a color density corresponding to an intensity of the acting first stress.

* * * * *